US011319276B2

(12) United States Patent
Treskow et al.

(10) Patent No.: US 11,319,276 B2
(45) Date of Patent: May 3, 2022

(54) PREPARATION OF DIESTERS OF (METH)ACRYLIC ACID FROM EPOXIDES

(71) Applicant: EVONIK OPERATIONS GMBH, Essen (DE)

(72) Inventors: Marcel Treskow, Darmstadt (DE); Martin Glock, Pfungstadt (DE); Günther Gräff, Bensheim (DE); Thorben Schütz, Alsbach-Hähnlein (DE); Steffen Krill, Mühltal (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/268,465

(22) PCT Filed: Aug. 15, 2019

(86) PCT No.: PCT/EP2019/071918
§ 371 (c)(1),
(2) Date: Feb. 13, 2021

(87) PCT Pub. No.: WO2020/035561
PCT Pub. Date: Feb. 20, 2020

(65) Prior Publication Data
US 2021/0179531 A1 Jun. 17, 2021

(30) Foreign Application Priority Data
Aug. 16, 2018 (EP) ..................... 18189280

(51) Int. Cl.
| | |
|---|---|
| *C07C 67/26* | (2006.01) |
| *B01J 27/132* | (2006.01) |
| *B01J 27/138* | (2006.01) |
| *B01J 31/02* | (2006.01) |
| *B01J 31/22* | (2006.01) |
| *C07C 67/54* | (2006.01) |

(52) U.S. Cl.
CPC ............ *C07C 67/26* (2013.01); *B01J 27/132* (2013.01); *B01J 27/138* (2013.01); *B01J 31/0239* (2013.01); *B01J 31/0244* (2013.01); *B01J 31/2234* (2013.01); *C07C 67/54* (2013.01); *B01J 2531/62* (2013.01)

(58) Field of Classification Search
CPC ......... C07C 67/26; C07C 69/16; C07C 69/54; C07C 67/54; B01J 2531/62; B01J 31/0239; B01J 27/132; B01J 27/138; B01J 31/0244; B01J 31/0267; B01J 31/0268; B01J 31/04; B01J 31/2234
See application file for complete search history.

(56) References Cited

U.S. PATENT DOCUMENTS

| | | |
|---|---|---|
| 1,710,424 A | 4/1929 | Loehr |
| 1,810,318 A | 6/1931 | Loehr |
| 1,817,425 A | 8/1931 | Stemmig et al. |
| 2,907,771 A | 10/1959 | Mills |
| 3,671,563 A | 6/1972 | Pfeiffer et al. |
| 5,623,086 A | 4/1997 | Perri et al. |
| 5,663,422 A | 9/1997 | Perri et al. |
| 2008/0255373 A1 | 10/2008 | Westfechtel |
| 2010/0266954 A1* | 10/2010 | Ito .................... C08F 220/28 430/285.1 |
| 2019/0352251 A1 | 11/2019 | Hartmann et al. |
| 2020/0331845 A1 | 10/2020 | Treskow et al. |
| 2021/0163439 A1 | 6/2021 | Treskow et al. |
| 2021/0179529 A1 | 6/2021 | Treskow et al. |
| 2021/0214297 A1 | 7/2021 | Bleith et al. |
| 2021/0269393 A1 | 9/2021 | Treskow et al. |

FOREIGN PATENT DOCUMENTS

| | | | |
|---|---|---|---|
| CN | 106582661 | | 4/2017 |
| EP | 2 055 699 | | 5/2009 |
| JP | 2017 128546 | | 7/2017 |
| JP | 2017128546 | * | 7/2017 |
| JP | 2018 008902 | | 1/2018 |

OTHER PUBLICATIONS

JP2017128546 translated (Year: 2017).*
International Search Report for corresponding international application PCT/EP2019/071918 filed Aug. 15, 2019.
Written Opinion of the International Searching Authority for corresponding international application PCT/EP2019/071918 filed Aug. 15, 2019.
International Preliminary Report on Patentability for corresponding international application PCT/EP2019/071918 filed Aug. 15, 2019.
European Search Report and Search Opinion for corresponding European application Ep 18189280.3 filed Aug. 16, 2018.
Büttner, et al., "Bifunctional One-Component Catalysts for the Addition of Carbon Dioxide to Epoxides," *CHEMCATCHEM* 7(3):459-467 (Dec. 2014).
Dalpozzo, et al., "1,2-Diacetates by epoxide ring opening promoted by erbium(III) triflate," *ARKIVOC (VI)*:67-73 (2006).
Fan, et al., "Tributlyphosphine-catalyzed ring-opening reaction of epoxides and aziridines with acetic anhydride," *Tetrahedron Letters* 44(23):4411-4413 (Jun. 2003).
Fogassy, et al., "Solvent-free ring opening reaction of epoxides using quaternary ammonium salts as catalyst," *Catalysis Communications* 10(5):557-560 (Jan. 2009).
Gilanizadeh, et al., "Heterogeneous acidic and eco-friendly reagents for mild and convient conversion of epoxides to 1,2-diacetates," *Journal of Chemical Research* 40:296-298 (May 2016).
"JEFFSOL® Alkylene Carbonates," Huntsman Corporation, pp. 1-36 (Aug. 2014); URL:https://web.archive.org/web/20140801094625if_/http://www. huntsman.com:80/performance_products/Media%20Library/global/files/jeffsol_alkylene_carbonates_brochure.pdf.

(Continued)

*Primary Examiner* — Brandon J Fetterolf
*Assistant Examiner* — Blaine G Doletski
(74) *Attorney, Agent, or Firm* — Law Office of Michael A. Sanzo, LLC

(57) ABSTRACT

The invention relates to a method for preparation of diesters from anhydrides of carboxylic acids.

20 Claims, No Drawings

(56) References Cited

OTHER PUBLICATIONS

"JEFFSOL® Alkylene Carbonates in Personal Care," Huntsman Technical Bulletin, pp. 1-2 (Jan. 2003); URL:http://www.huntsman.com/performance_products/Media/JEFFSOL_Alkylene_Carbonates_in_Personal_Care.pdf.

Khusnutdinov, et al., "Reactions of Diols with Dimethyl Carbonate in the Presence of $W(CO)_6$ and $Co_2(CO)_8$," *Russian Journal of Organic Chemistry* 50(7):948-952 (Jul. 2014).

Rahman, et al., "Actinobolin via the Anomeric Effect," *J. Am. Chem. Soc.* 107(19):5576-5578 (Sep. 1985).

Ramesh, et al., "Zeolite Catalyzed Ring Opening of Epoxides to Acetylated Diols With Acetic Anhydride," *Synthetic Communications* 31(17):2599-2604 (2001).

Schwenk, et al., "Synthese von Polyestern aus Dicarbonsäureanhydriden und Epoxyden oder cyclischen Carbonaten von Diolen," *Makromolekulare Chemie* 51:53-69 (1962).

Shvets, et al., "Kinetic and Mechanism of Pyridine-Catalyzed Reaction of Ethylene Oxide With Acetic Anhydride," Translated from *Kinet. Katal.* 16(3):785-788 (May-Jun. 1975).

Werner, et al., "Phosphorus-based Bifunctional Organocatalysts for the Addition of Carbon Dioxide and Epoxides," *ChemSusChem* 7(12):3268-3271 (Oct. 2014).

Werner, et al., Supporting Information ., "Phosphorus-based Bifunctional Organocatalysts for the Addition of Carbon Dioxide and Epoxides," *ChemSusChem* 7(12):3268-3271 (Oct. 2014); pp. 1-58.

Yoshino, et al., "Synthetic Studies with Carbonates. Part 6," *J. Chem. Soc., Perkins Trans.* 1:1266-1272 (1977).

Zeynizadeh, et al., "A Green Protocol for Catalytic Conversion of Epoxides to 1,2-Diacetoxy Esters with Phosphomolybdic Acid Alone or Its Supported on Silica Gel," *Bull. Korean Chem.* 31(9):2644-2648 (2010).

U.S. Appl. No. 16/479,497, filed Jul. 19, 2019, U.S. Pat. No. 2019/0352251 A1, Nov. 21, 2019, Hartmann.
U.S. Appl. No. 16/753,287, filed Apr. 2, 2020, U.S. Pat. No. 2020/0331845 A1, Oct. 22, 2020, Treskow.
U.S. Appl. No. 16/973,995, filed Dec. 10, 2020, Treskow.
U.S. Appl. No. 17/057,659, filed Nov. 21, 2020, Bleith.
U.S. Appl. No. 17/260,223, filed Jan. 14, 2021, Treskow.
U.S. Appl. No. 17/260,226, filed Jan. 14, 2021, Treskow.
U.S. Appl. No. 17/262,735, filed Jan. 24, 2021, Treskow.
U.S. Appl. No. 17/268,463, filed Feb. 13, 2021, Treskow.

* cited by examiner

PREPARATION OF DIESTERS OF (METH)ACRYLIC ACID FROM EPOXIDES

CROSS REFERENCE TO RELATED APPLICATIONS

The present application is US national stage of international application PCT/EP2019/071918, which had an international filing date of Aug. 15, 2019 and which was published on Feb. 20, 2020. The application claims priority to EP 18189280.3, filed on Aug. 16, 2018. The contents of the priority application is hereby incorporated by reference in its entirety.

The invention relates to a method for preparation of diesters of carboxylic acids from epoxides.

(Meth)acrylic acid diesters are commonly used as monomers for the preparation of various poly(meth)acrylates and of the corresponding copolymers. Accordingly, a variety of methods of obtaining (meth)acrylic acid esters are known. These methods include, in particular, transesterification reactions in which methyl methacrylate is reacted with a diol. A further common possibility is acylation of a diol with (meth)acrylic acid anhydride.

Acylation of diols with (meth)acrylic acid anhydrides and sulfonic acid anhydrides, in particular with methacrylic acid anhydride (MAAH) is typically carried out in the presence of acids such as sulfuric acid. Under these conditions, undesired reactions such as polymerisation of the anhydrides commonly take place and therefore the product yields of the (meth)acrylic acid diesters are only moderate. Additionally, preparation of (meth)acrylic acid diesters of sterically hindered diols is known to suffer from low reaction yields, because such diols not only have a low reactivity towards (meth)acrylic acid anhydrides but also tend to undergo undesired dehydration under typically employed reaction conditions.

For these reasons, in order to achieve a reasonably high conversion of sterically hindered diols, (meth)acrylic acid anhydrides are commonly used in a large excess. This is disadvantageous from economic and environmental points of view since (meth)acrylic acid anhydrides are rather expensive and recovery of the unreacted excess of the anhydrides is difficult. For instance, preparation of ethylene glycol dimethacrylate, which is a commonly used monomer for crosslinking, typically requires a large excess of the MAAH. Furthermore, acylation of one equivalent of alcoholic functionalities usually requires at least one equivalent of the anhydride. In other words, merely less than 50 wt.-% of employed MAAH becomes incorporated into the desired product, the rest being converted to undesired methacrylic acid. The methacrylic acid needs to be separated from the product mixture in a separate washing step which generates a considerable amount of aqueous waste.

U.S. Pat. Nos. 1,710,424, 1,810,318 and 1,817,425 describe preparation of diesters of polyalkylene glycols at elevated temperatures by reacting an olefin oxide with an organic carboxylic acid in the presence of sulfuric acid as a catalyst. Preparation of (meth)acrylic acid diesters is not mentioned in these documents and these protocols are not suitable for such purpose.

G. Fogassy et al. (*Catalysis Communications* 2009, No. 10, 557-560) describe a solvent-free ring opening reaction of epoxides with carboxylic acid anhydrides using quaternary ammonium salts as a catalyst. The publication only describes use of non-polymerisable anhydrides of acetic acid, propionic acid and butyric acid. Preparation of (meth) acrylic acid diesters is not mentioned in this document and the protocol is not suitable for this purpose.

B. Zeynizadeh et al. (*Bull. Korean Chem. Soc.* 2010, Vol. 31, No. 9, 2644-2648) describes a green protocol for catalytic conversion of epoxides to 1,2-diacetoxy esters with phosphomolybdic acid. Again, the authors do not mention preparation of (meth)acrylic acid diesters.

R. Dalpozo et al. (ARKIVOC, 2006, Vol. 6, 67-73) describes a protocol for the synthesis of 1,2-diacetates by epoxide ring opening with acetic anhydride promoted by erbium(III) triflate. The employed stoichiometry (epoxide: anhydride) is 1:2. The protocol is not suitable for use with a (meth)acrylic acid anhydride or with more reactive epoxides, even at elevated temperatures. Furthermore the purchase costs of erbium (III) are high, which prevents its use on an industrial scale.

Ren-Hua et al. (Tetrahedron Letters, 2003, Vol. 44, 23, 4411-4413) describes a protocol for tributylphosphine-catalyzed ring-opening reaction of epoxides and aziridines with acetic anhydride. The protocol is very efficient for acetic anhydride, but cannot be applied with polymerisable anhydrides such as (meth)acrylic anhydride due to polymerization at the required reaction temperature (110° C.). At lower reaction temperatures this procedure gives poor product yields and requires a very high catalyst loads of at least 10 mol.-%.

P. Ramesh et al. (Synthetic Communications, 2001, Vol. 31, 17, 2599-2604) describe zeolite catalyzed ring opening of epoxides to acetylated diols with acetic anhydride. This protocol requires a fivefold excess of anhydride, which is disadvantageous and industrial scale. Furthermore commercially available zeolite show only a moderate catalytic activity with MAAH.

M. Gilanizadeh et al. (Journal of Chemical Research, 2016, Vol. 40, 5, 296-298) describe use of catalysts such as Na2HPO4 and NaHSO4 for a conversion of epoxides to 1,2-diacetates. Again, the process required excess of 10.5 eq. anhydride. Although the described protocol works well with acetic anhydride, undesired polymerisation takes place if (meth)acrylic acid anhydrides are used.

Md. A. Rahman et al. (J. Am. Chem. Soc. 1985, Vol. 107, 5576-5578) describes conversion of an epoxide with tetrabutylammonium acetate as a catalyst and acetic anhydride in 70% yield. No experimental details about stoichiometric employed are disclosed.

U.S. Pat. No. 5,623,086 describe a process for production of 1,2-bisacyloxylates, by acylation of epoxides with carboxylic anhydrides in the presence of a catalytic composition containing a tertiary amine and a carboxylic acid which may be generated in situ. Preparation of (meth)acrylic acid diesters is not mentioned in this document.

V. F. Shveets et al. (Kinet. Katal. 1975, 16, 785) describes a pyridine-catalyzed reaction of ethylene oxide with acetic anhydride. The latter is employed as a solvent and concentration of epoxide in the reaction mixture is as low as 1 mol/L. At 105° C. product yields of up to 93.5% yield are reported.

T. Yoshino (J. Chem. Soc., Perkin Trans. 1, 1977, 1266-1272) describes acylation of cyclohexane oxide with acetic anhydride and benzoic anhydride in the presence of tetraalkylammonium salts at 130° C. Polymerisable anhydrides such as (meth)acrylic acid anhydrides are not mentioned.

In view of the above-described technical problems of the prior art it has been the purpose of the present invention to develop an efficient industrially applicable process for preparation of (meth)acrylic acid diesters from the corresponding anhydrides. Such process should ideally offer the following advantages:

high product yields and high conversions of (meth)acrylic acid diesters
short reaction times
low excess of the anhydride
low amounts of the catalysts which, if desired, can be easily separated from the resulting product.

Additionally, the process should be suitable for preparation of diesters of (meth)acrylic acids on an industrial scale in an efficient and inexpensive manner.

The present invention is based on a surprising finding that said diesters can be obtained in excellent product yields by reacting an epoxide of general formula (III)

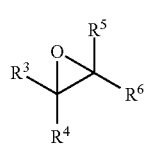
(III)

with a (meth) acrylic acid anhydride of general Formula (II)

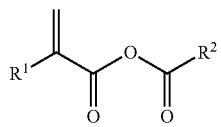
(II)

in the presence of a catalyst in combination with a co-catalyst, the catalyst being a first catalyst, a second catalyst or a combination of both, wherein
the first catalyst is a halide of magnesium or a trifluoromethanesulfonate of a rare earth element; and
the second catalyst is a chromium (III) salt,
and the co-catalyst is selected from the group consisting of a tertiary amine, a quaternary ammonium salt, a tertiary phosphine, and a quaternary phosphonium salt.

In other words, according to the present invention, the diester of general Formula (I) can be obtained in a product yield of at least 40 area %, as determined by gas chromatography, after a reaction time of not more than 3 hours, typically at a reaction temperature of below 70° C.

Accordingly, one aspect of the present invention relates to a process for preparation of a diester of general Formula (I)

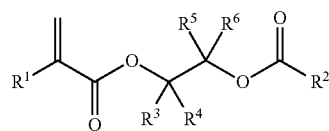
(I)

$R^1$ being a hydrogen atom or a methyl group,
$R^2$ to $R^6$ being independently selected from hydrogen atoms or optionally substituted aliphatic or aromatic substituents having up to 17 carbon atoms, preferably an optionally substituted alkyl, cycloalkyl, alkenyl, or alkadienyl substituents having up to 17 carbon atoms, more preferably an alkyl, cycloalkyl, alkenyl, or alkadienyl substituents having up to 17 carbon atoms optionally substituted with one substituent $R^7$; and wherein the process comprises at least the following process step (a):
(a) a reaction between an anhydride of general Formula (II)

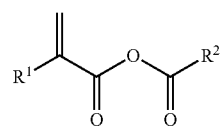
(II)

and an epoxide of general Formula (III)

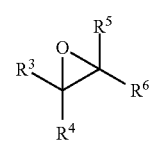
(III)

to deliver a product mixture comprising the diester of general Formula (I).

$R^3$ and $R^5$ and/or $R^4$ and $R^6$ may build a ring structure while the remaining substituents may be independently selected from hydrogen atoms and optionally substituted aliphatic or aromatic substituents having up to 17 carbon atoms. Similarly, $R^3$ and $R^4$ may build a ring structure, as occurring in methylenecyclohexane epoxide and optionally substituted derivatives thereof.

The reaction is carried out in the presence of a co-catalyst and at least one of the following:
a first catalyst comprising a halide of magnesium or a trifluoromethanesulfonate of a rare earth element; and
a second catalyst comprising a chromium (III) salt, preferably a chromium (III) carboxylate.

According to the present invention, the co-catalyst is selected from the group consisting of a tertiary amine, a quaternary ammonium salt, a tertiary phosphine, and a quaternary phosphonium salt.

The term "catalytic system" as used in the present application refers to a combination of a co-catalyst with a first catalyst and/or with a second catalyst.

The substituent $R^7$ may be selected from a halogen atom, —CN, —SCN, —OCN, and —NCO. The terms "halo" and "halide"/"halogen" as used herein refer to functional groups comprising a halogen atom in any oxidation state.

For example, the halogen atom may be selected from the group consisting of fluorine atom, chlorine atom, bromine atom, iodine atom, chlorate and perchlorate.

The term "aliphatic substituent" as used herein, includes saturated or unsaturated, branched or unbranched aliphatic univalent substituents. In the present application, aliphatic substituent is intended to include but is not limited to alkyl, alkenyl, alkadienyl, and cycloalkyl substituents. According to the present invention, the aliphatic substituent may have up to 17 carbon atoms, preferably 1 to 10 carbon atoms, most preferably 1 to 6 carbon atoms.

The term "alkyl" used is the present application relates a saturated branched or unbranched aliphatic univalent substituent. The alkyl substituent has up to 17 carbon atoms, preferably 1 to 10 carbon atoms, most preferably 1 to 6 carbon atoms. Examples of the alkyl substituent include but are not limited to methyl, ethyl, n-propyl, iso-propyl, n-butyl, iso-butyl, sec-butyl, iso-butyl, n-pentyl and n-hexyl.

The term "cycloalkyl" as used herein, refers to an univalent monocyclic, bicyclic, or tricyclic substituent, which may be saturated or partially saturated, i.e. possesses one or more double bonds. Monocyclic substituents are exemplified by a saturated cyclic hydrocarbon group containing from 3 to 8 carbon atoms. Examples of monocyclic cycloalkyl substituents include cyclopropyl, cyclobutyl, cyclopentyl, cyclopentenyl, cyclohexyl, cyclohexenyl, cycloheptyl and cyclooctyl. Bicyclic fused cycloalkyl substituents are exemplified by a cycloalkyl ring fused to another cycloalkyl ring. Examples of bicyclic cycloalkyl substituents include, but are not limited to decalin, 1,2,3,7,8,8a-hexahydro-naphthalene, and the like. Tricyclic cycloalkyl substituents are exemplified by a cycloalkyl bicyclic fused ring fused to an additional cycloalkyl substituent.

The term "alkenyl" as used is the present application is an unsaturated branched or unbranched aliphatic univalent substituent having a double bond between two adjacent carbon atoms. The alkenyl substituent has 2 to 17 carbon atoms, preferably 2 to 10 carbon atoms, most preferably 2 to 6 carbon atoms. Examples of the alkenyl substituent include but are not limited to vinyl, 1-methylvinyl, 1-propenyl, 2-propenyl, methylvinyl, 1-butenyl, 2-butenyl, 3-butenyl, 2-methyl-1-propenyl, 2-methyl-2-propenyl, 2-pentenyl and 2-hexenyl.

The term "alkadienyl" as used is the present application is an unsaturated branched or unbranched aliphatic univalent substituent having two double bonds between two adjacent carbon atoms. The alkenyl substituent has 4 to 17 carbon atoms, preferably 4 to 12 carbon atoms, most preferably 4 to 10 carbon atoms. Accordingly, examples of the alkadienyl substituent include but are not limited to 2,4-pentadienyl, 2,4-hexadienyl, 4-methyl-2,4-pentadienyl, 2,4-heptadienyl, 2,6-heptadienyl, 3-methyl-2,4-hexadienyl, 2,6-octadienyl, 3-methyl-2,6-heptadienyl, 2-methyl-2,4-heptadienyl, 2,8-nonadienyl, 3-methyl-2,6-octadienyl, 2,6-decadienyl, 2,9-decadienyl and 3,7-dimethyl-2,6-octadienyl substituents.

As used herein, the term "aromatic substituent" is intended to mean any stable monocyclic, bicyclic or polycyclic carbon ring of up to 10 atoms in each ring, wherein at least one ring is aromatic, and may be unsubstituted or substituted. Examples of such aromatic substituents include phenyl, p-toluenyl (4-methylphenyl), naphthyl, tetrahydronaphthyl, indanyl, biphenyl, phenanthryl, anthryl or acenaphthyl. In cases where the aromatic substituent is bicyclic and one ring is non-aromatic, it is understood that attachment is via the aromatic ring.

The term "(meth)acrylate" as used in the present application may refer to a methacrylate or an acrylate.

The reaction in the process step (a) can be summarised by the following reaction scheme:

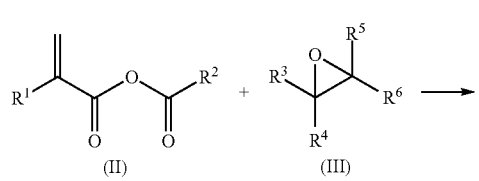

-continued

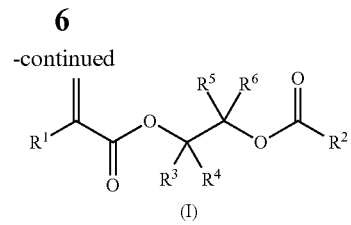

As can be readily noted from the reaction scheme, substantially entire anhydride of general Formula (II) becomes incorporated into the resulting diester of general Formula (I). In other words, substantially no undesired formation of free acids from the acid anhydride of general Formula (II) takes place. Thus, the process offers a decisive advantage over a classical acylation of diols with acid anhydrides, where acylation of one equivalent of hydroxyl groups leads to undesired formation of one equivalent of free acids as a side-product.

In most common embodiments of the present invention, the carboxylic acid anhydride is a symmetrical anhydride as represented by formula (IIa), wherein the substituents $R^8$ and $R^9$ are identical.

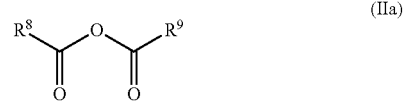

Notwithstanding the above, the carboxylic acid anhydride represented by the Formula (IIa) may also be a mixed anhydride (i.e. the substituents $R^8$ and $R^9$ are different from each other).

The (meth)acrylic acid anhydride of Formula (II)

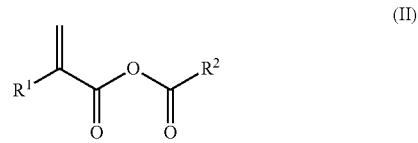

may be an acrylic acid anhydride ($R^1$ is a hydrogen atom) or a methacrylic acid anhydride ($R^1$ is a methyl group). For instance, the (meth)acrylic acid anhydride of Formula (II) may be a symmetrical anhydride i.e. if the substituent $R^1$ is a hydrogen atom and $R^2$ is represented by a vinyl group, the (meth)acrylic acid anhydride of Formula (II) is acrylic acid anhydride. Accordingly, if the substituent $R^1$ is a methyl group and $R^2$ is represented by a 1-methylvinyl group, so that the (meth)acrylic acid anhydride of Formula (II) is MAAH.

In other words, in one preferred embodiment the (meth)acrylic acid anhydride of Formula (II) is selected from acrylic acid anhydride and MAAH as described by the following Formula (IIb):

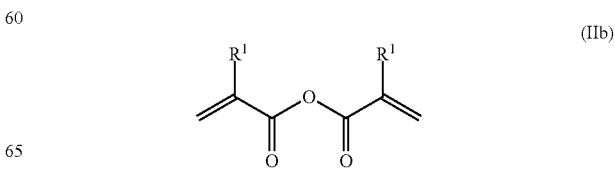

wherein $R^1$ is a hydrogen atom or a methyl group.

As indicated in the above, the (meth)acrylic acid anhydride of Formula (II) may be a mixed anhydride. In this embodiment, the substituent $R^2$ is not particularly limited and may be an optionally substituted aliphatic or aromatic substituent having up to 17 carbon atoms, preferably an optionally substituted aliphatic substituent having up to 17 carbon atoms, more preferably an optionally substituted alkyl, cycloalkyl, alkenyl, or alkadienyl substituent having up to 17 carbon atoms, even more preferably an alkyl, alkenyl, or alkadienyl substituent having up to 17 carbon atoms optionally substituted with one $R^7$ as defined above.

For instance, the substituent $R^2$ may be selected from one of the following:

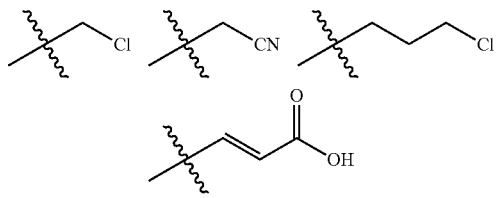

Further examples of the substituent $R^2$ include e.g. methyl, n-pentyl, n-undecyl, n-heptadecyl, (Z)-8-n-heptadecyl.

Due a high catalytic activity of the first catalyst and/or the second catalyst in combination with the co-catalyst as specified above the choice of epoxide of general Formula (III) is not limited. The process step (a) can be carried out substantially with any epoxide of general Formula (III) thereby delivering the desired diesters of general Formula (I) in good product yields. For instance, the epoxide of general Formula (III) may be selected from the group consisting of ethylene oxide, propylene oxide (PO), 1-hexene oxide, cyclohexene oxide, cyclopentene oxide, 1-butene oxide, 2-butene oxide, isobutene oxide, styrene oxide and glycidyl methacrylate.

The inventors surprisingly found that the first catalyst and the second catalyst, if employed in combination, act synergistically. Therefore, it is highly advantageous that the process step (a) is carried out in the presence of the co-catalyst, the first catalyst and the second catalyst.

The first catalyst comprises a halide of magnesium or a trifluoromethanesulfonate of a rare earth element. The term "rare earth element" as used herein refers to an element selected from cerium, dysprosium, erbium, europium, gadolinium, holmium, lanthanum, lutetium, neodymium, praseodymium, promethium, samarium, scandium, terbium, thulium, ytterbium and yttrium. In a particularly preferred embodiment, the term "rare earth element" refers to an element selected from lanthanum, ytterbium, yttrium and scandium.

The catalytic activity of the first catalyst is particularly high if the halide is selected from fluoride, chloride, bromide, iodide, and perchlorate. In a particularly preferred embodiment, the salt may be selected from a chloride, bromide, and iodide.

The catalytic activity of the first catalyst is particularly high when the first catalyst comprises a trifluoromethanesulfonate of a rare earth element. In particular, use of the first catalyst selected from the group consisting of magnesium bromide, magnesium iodide, magnesium chloride, magnesium perchlorate, lanthanum (III) trifluoromethanesulfonate, ytterbium (III) trifluoromethanesulfonate, yttrium (III) trifluoromethanesulfonate and scandium (III) trifluoromethanesulfonate tends to lead to particularly high product yields of the diester of general Formula (I). The first catalyst may be used in an anhydrous form or as a hydrate.

As already mentioned above, the co-catalyst may be selected from the group consisting of a tertiary amine, a quaternary ammonium salt, a tertiary phosphine, and a quaternary phosphonium salt.

The choice of a tertiary amine is not particularly limited and compounds such as pyridine, triethylamine, diisopropylethylamine, dimethylaminopyridine (DMAP) etc. can be advantageously employed as a co-catalyst.

The choice of a quaternary ammonium salt is not particularly limited either. For instance, quaternary ammonium salts such as tetrabutylammonium chloride, tetrabutylammonium bromide, tetraethylammonium chloride, tetrabutylammonium acetate, tetramethylammonium chloride, tetrapentylammonium bromide, cetyltrimethylammonium bromide, 1-butyl-3-methyl-imidazolyl chloride, cetylpyridinium chloride and triethylbenzylammonium chloride (TEBAC) can be advantageously used in the process step (a). Examples of quaternary ammonium salts further include tetra(C1-16 alkyl) ammonium salts, tetra(C6-24)aryl ammonium salts, and tetra(C7-24 arylalkylene) ammonium salts. Examples of specific tetra(C1-16 alkyl) ammonium salts include tetraethylammonium bromide, tetrapropylammonium bromide, tetrabutylammonium iodide, tetrabutylammonium bromide, tetrabutylammonium chloride, tetrabutylammonium fluoride, tetrabutylammonium acetate, tetrahexylammonium chloride, tetraheptylammonium chloride, benzyltriethylammonium bromide, hexadecyltrimethylammonium bromide, ALIQUAT 336 (methyltrioctylammonium chloride), ADOGEN 464 (methyltri(C8-C10 alkyl) ammonium chloride), and 1,6-bis(tributylammonium) hexane dibromide. Examples of tetra(C6-24)aryl ammonium salts include tetraphenylammonium bromide.

The choice of a tertiary phosphine is not particularly limited. Typical tertiary phosphines which may be employed in accordance with the present invention include e.g. triphenylphosphine, tri(4-chlorophenyl) phosphine, tri-(3-methoxyphenyl)phosphine, tri-(2-tolyl) phosphine, tri-(a-naphthyl) phosphine, diphenyl-4-bromophenylphosphine, diphenyl-4-tolylphosphine, phenyl-4-tolyl-4-methoxyphenylphosphine, tris-2 (dimethylaminomethylphenyl)phosphine, diphenyl 4-(diphenylphosphinophenyl)phosphine, phenyldimethylphosphine, phenyldiethylphosphine, dimethyl-2-(dimethylphosphino)ethvlphosphine, tributylphosphine, trihexylphosphine etc.

The choice of a quaternary phosphonium salt is not particularly limited. Examples of suitable quaternary phosphonium salts further include tetrabutylphosphonium bromide, tetrabutylphosphonium chloride, tetraphenylphosphonium chloride methylbenzyltriphenylphosphonium bromide, tetraphenylphosphonium bromide, and trihexyltetradecylphosphonium chloride.

The second catalyst is a chromium (III) salt and typically a chromium (III) carboxylate such as chromium (III) 2-ethylhexanoate, chromium (III) heptanoate, chromium (III) acetate or chromium (III) methacrylate.

Due to a high activity of the employed catalytic system, the reaction between the anhydride of general Formula (II) and the epoxide of general Formula (III) in the process step (a) proceeds smoothly even if the first catalyst and/or the second catalyst and the co-catalyst are present in relatively low amounts. Nevertheless, by using said catalysts and the co-catalyst in higher amounts, the reaction time during the process step (a) can be additionally reduced.

Depending on the reactivity of the epoxide of general Formula (III), the total amount of the first catalyst in the process step (a) is typically chosen to be between 0.001 mol.-% and 10 mol.-%, more preferably between 0.01 mol.-% and 1.0 mol.-%, even more preferably between 0.1 mol.-% and 0.5 mol.-%, based on the amount of the epoxide of general Formula (III).

The total amount of the second catalyst in the process step (a) is typically chosen to be between 0.001 mol.-% and 10 mol.-%, more preferably between 0.01 mol.-% and 1.0 mol.-%, even more preferably between 0.1 mol.-% and 0.5 mol.-%, based on the amount of the epoxide of the general Formula (III).

The total amount of the co-catalyst in the process step (a) is typically chosen to be between 0.001 mol.-% and 10 mol.-%, more preferably between 0.01 mol.-% and 1.0 mol.-%, even more preferably between 0.1 mol.-% and 0.5 mol.-%, based on the amount of the epoxide of general Formula (III).

The reaction solvent for the process step (a) is not particularly limited, as long as the solvent cannot undergo a chemical reaction with the anhydride of general Formula (II) and its boiling point allows the process step (a) to be carried out at the desired temperature. Advantageously, however, the process step (a) is carried out in the absence of any solvent.

Furthermore, they are substantially no limitations regarding the order of addition of reagents in the process step (a). In one embodiment, the co-catalyst and a first catalyst and/or the second catalyst may be first dispersed in the epoxide of general Formula (III) and, subsequently, the anhydride of general Formula (II) is added thereto Alternatively, the co-catalyst and a first catalyst and/or the second catalyst may first be dispersed in the anhydride of general Formula (II), followed by addition of the epoxide of general Formula (III) to the resulting dispersion.

In some embodiments, it is also possible to prepare a mixture of the anhydride of general Formula (II) with the epoxide of general Formula (III) first and start the reaction by adding the co-catalyst and a first catalyst and/or the second catalyst thereto However, use of this procedure on an industrial scale is generally more difficult.

The optimal reaction temperature during the process step (a) can be readily adjusted by a skilled person depending on the reactivity of the epoxide of general Formula (III) and of the anhydride of general Formula (II). Typically, the reaction temperature during the process step (a) is kept between 20° C. and 140° C., preferably between 40° C. and 110° C., more preferably between 60° C. and 90° C.

Due to a high catalytic activity of the employed catalysts, the reaction time for the process step (a) typically ranges between 10 minutes and 10 hours, usually between 30 minutes and 4 hours. As will be readily appreciated by a skilled person, the reaction time for the process step (a) can be adjusted by varying the reaction temperature and the amount of the catalysts.

The molar ratio anhydride of general Formula (II):epoxide of general Formula (III) in the process step (a) is between 5:1 and 1:0.1, preferably between 3:1 and 1:0.5, more preferably between 2:1 and 1:1, even more preferably between 1.5:1 and 1:1.

The reaction between the anhydride of general Formula (II) and the epoxide of general Formula (III) in the process step (a) is often carried out in a presence of a slight excess of the anhydride, e.g. of at least 10 mol. % excess, or of at least 20 mol. % excess, based on the amount of the epoxide of general Formula (III). In order to separate the unreacted excess of the anhydride of general Formula (II) from the obtained diester of general Formula (I), an auxiliary alcohol may be added to the product mixture obtained in the process step (a). Under these conditions, a product mixture comprising the desired diester of general Formula (I) and an ester of the auxiliary alcohol is formed. Subsequently, the ester of the auxiliary alcohol can be separated from this product mixture, typically by distillation.

Hence, in this embodiment, the process of the present invention can be carried out as follows:

(a) reaction between the anhydride of general Formula (II) and the epoxide of general Formula (III), whereby a product mixture comprising the diester of general Formula (I) is formed;

(b) addition of an auxiliary alcohol to the product mixture obtained in the process step (a), whereby a product mixture comprising the diester of general Formula (I) and an ester of the auxiliary alcohol is formed; and (c) removal of the ester of the auxiliary alcohol from the product mixture obtained in the process step (b).

The auxiliary alcohol is usually a primary or a secondary alcohol. Since it has a high reactivity, it smoothly reacts with the unreacted anhydride of general Formula (II) in the process step (b) thereby forming a methacrylic acid ester of the auxiliary alcohol. For the sake of an easy separation of the ester of the auxiliary alcohol in process step (c) by distillation, it is preferred that the auxiliary alcohol has a boiling point of not more than 150° C., preferably not more than 120° C., more preferably not more than 80° C., measured at a pressure of $10^5$ Pa. For instance, the auxiliary alcohol can be advantageously selected from methanol, ethanol, n-propanol, iso-propanol or a mixture thereof, wherein methanol is particularly preferred.

The following examples will illustrate the present invention in a greater detail but are not meant to be limiting.

EXAMPLES

Abbreviations

AAH acrylic acid anhydride $Ac_2O$ acetic acid anhydride

CHO cyclohexene oxide

DMAP dimethylaminopyridine

EO ethylene oxide

GC gas chromatography

MAAH methacrylic acid anhydride

MSAA methanesulfonic acid anhydride

PO propylene oxide

PPG polypropylene glycol

SO styrene oxide

TEBAC triethylbenzylammonium chloride

THF tetrahydrofurane

GENERAL REMARKS

All materials were used as commercially available without further purification.

All employed (meth)acrylic anhydrides were stabilized with 2000 ppm (by weight) of 2,4-dimethyl-6-tert-butylphenol.

Example 1 (Comparative): Reaction Between MAAH and PO in the Absence of any Catalyst

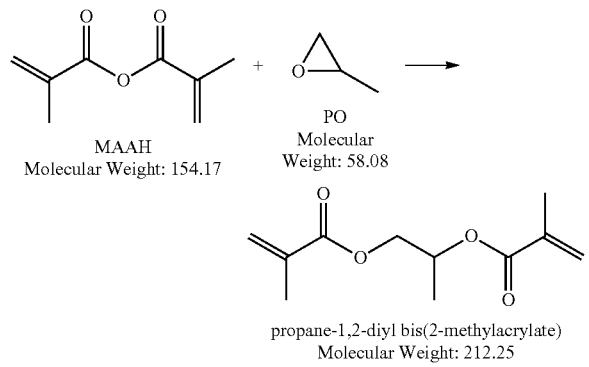

MAAH
Molecular Weight: 154.17

PO
Molecular Weight: 58.08 propane-1,2-diyl bis(2-methylacrylate)
Molecular Weight: 212.25

In a 15 ml pressure tube with magnetic stirrer, 3.08 g (0.02 mol) methacrylic acid anhydride (MAAH) were placed and 1.16 g (0.02 mol) propylene oxide (PO) were carefully added dropwise. No exothermic reaction could be monitored. The tube was sealed with a Teflon® plug and heated for 3 h to 70° C.

Subsequently, the sample was cooled to room temperature and analyzed using gas chromatography (GC).

Result (GC area-%):

| | |
|---|---|
| PO | 27.30% |
| MAAH | 70.81% |
| product: | none |

No uncatalysed reaction between MAAH and PO took place.

Examples 2-7 (Comparative): Reaction Between MAAH and PO in Presence of a First Catalyst, a Second Catalyst or a Co-Catalyst A first catalyst, a second catalyst or a co-catalyst specified in Table 1 was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for 3 h to 70° C.

After the time had elapsed, the sample was cooled to room temperature and analyzed using GC.

TABLE 1

Catalyst tested for the reaction between MAAH and PO

| Ex. | Catalyst/co-catalyst | Amount | Color | MAAH, GC area % | PO, GC area % | Product, GC area-% |
|---|---|---|---|---|---|---|
| 2 | MgBr$_2$*6 H$_2$O | 0.006 g (0.1 mol.-%, rel. to PO) | colorless | 69.59 | 26.04 | 1.43 |
| 3 | lanthanum (III) triflate | 0.012 g (0.1 mol.-%, rel. to PO) | colorless | 68.95 | 16.07 | 0.51 |
| 4 | triethylbenzyl-ammonium chloride (TEBAC) | 0.091 g (2 mol.-%, rel. to PO) | orange | 31.28 | 15.57 | 33.05 |

TABLE 1-continued

Catalyst tested for the reaction between MAAH and PO

| Ex. | Catalyst/co-catalyst | Amount | Color | MAAH, GC area % | PO, GC area % | Product, GC area-% |
|---|---|---|---|---|---|---|
| 5 | H$_2$SO$_4$ | 0.020 g (1 mol.-%, rel. to PO) | colorless | 67.78 | 23.31 | 0.29 |
| 6 | Cr(III) 2-ethyl-hexanoate (7 wt.-%) in polypropylene glycol 400 | 0.064 g (1.5 wt.-% rel. to entire batch) | green | 72.50 | 18.52 | 2.14 |
| 7 | DMAP | 0.049 g (2 mol.-% rel. to PO) | black | 43.20 | 18.60 | 28.90 |

DMAP and TEBAC showed some catalytic activity so that minor amounts of the desired product could be detected.

Furthermore, small amounts of the desired product were detected in the presence of chromium (III) carboxylates and MgBr$_2$. These results are surprising, because MgBr$_2$ is known to be a highly active catalyst for activation of anhydrides.

Examples 8-14: Reaction Between MAAH and PO in Presence of a Catalyst/Co-Catalyst A catalyst/co-catalyst as specified in Table 2 in combination listed in Table 3 was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for 3 h to 70° C.

After the time had elapsed, the sample was cooled to room temperature and analyzed using GC.

TABLE 2

Catalysts/co-catalysts for reaction between MAAH and PO in Table 3.

| Nr. | Catalyst/co-catalyst | Amount |
|---|---|---|
| 1 | MgBr$_2$*6 H$_2$O | 0.006 g (0.1 mol.-%, rel. to PO) |
| 2 | TEBAC | 0.091 g (2 mol.-%, rel. to PO) |
| 3 | Cr(III) 2-ethyl-hexanoate (7 wt.-%) in polypropylene glycol 400 | 0.064 g (1.5 wt.-% rel. to entire batch) |
| 4 | dimethylaminopyridine (DMAP) | 0.049 g (2 mol.-% rel. to PO) |

TABLE 3

Catalyst/co-catalyst combinations tested for the reaction between MAAH and PO

| Ex. | Catalytic system | Color | Comment | MAAH GC area-% | PO GC area-% | Product GC area-% |
|---|---|---|---|---|---|---|
| 8 | 1 + 3 MgBr$_2$*6 H$_2$O/Cr$^{3+}$ | green | | 61.431 | 15.638 | 4.051 |
| 9 | 1 + 2 MgBr$_2$*6 H$_2$O/TEBAC | colorless | | 32.735 | 12.604 | 45.705 |
| 10 | 3 + 4 Cr$^{3+}$/DMAP | black | solids precipitated | 0.093 | 1.652 | 83.862 |

TABLE 3-continued

Catalyst/co-catalyst combinations
tested for the reaction between MAAH and PO

| Ex. | Catalytic system | Color | Comment | MAAH GC area-% | PO GC area-% | Product GC area-% |
|---|---|---|---|---|---|---|
| 11 | 1 + 3 + 4 MgBr$_2$*6 H$_2$O/ Cr$^{3+}$/DMAP | black | solids precipitated | 0.156 | 1.567 | 87.153 |
| 12 | 1 + 2 + 4 MgBr$_2$*6 H$_2$O/ TEBAC/DMAP | brown | | 18.431 | 10.151 | 54.827 |
| 13 | 1 + 2 + 3 MgBr$_2$*6 H$_2$O/ TEBAC/Cr$^{3+}$ | black | solid precipitated | 0.082 | 1.195 | 89.643 |
| 14 | 2 + 3 + 4 TEBAC/Cr$^{3+}$/ DMAP | black | | 0.028 | 0.632 | 82.181 |

Catalytic systems comprising a combination of a co-catalyst with a first catalyst and/or with the second catalyst show a good catalytic activity. In contrast, a combination of a first catalyst and a second catalyst is not catalytically active in the absence of a co-catalyst.

Examples 15-18: Reaction Between MAAH and PO in Presence of Varying Amounts of a Chromium Catalyst A catalyst/co-catalyst mixture, containing different amounts of MgBr$_2$ with a Cr(III) salt and TEBAC selected from Table 4 was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for 3 h to 70° C.

After the time had elapsed, the sample was cooled to room temperature and analyzed using GC.

TABLE 4

Catalytic systems for the reaction between MAAH and PO in Table 5

| Nr. | | Catalyst/co-catalyst | |
|---|---|---|---|
| 1 | 0.0058 g | MgBr$_2$*6 H$_2$O | 0.1 mol.-% rel. to PO |
|   | 0.0911 g | TEBAC | 2 mol.-% rel. to PO |
|   | 0.0424 g | Cr(III) * | 1 wt.-% rel. to entire batch |
| 2 | 0.0058 g | MgBr$_2$*6 H$_2$O | 0.1 mol.-% rel. to PO |
|   | 0.0911 g | TEBAC | 2 mol.-% rel. to PO |
|   | 0.0212 g | Cr(III) * | 0.5 wt.-% rel. to entire batch |
| 3 | 0.0058 g | MgBr$_2$*6 H$_2$O | 0.1 mol.-% rel. to PO |
|   | 0.0456 g | TEBAC | 2 mol.-% rel. to PO |
|   | 0.0637 g | Cr(III) * | 1.5 wt.-% rel. to entire batch |
| 4 | 0.0058 g | MgBr$_2$*6 H$_2$O | 0.1 mol.-% rel. to PO |
|   | 0.0456 g | TEBAC | 2 mol.-% rel. to PO |
|   | 0.0318 g | Cr(III) * | 0.75 wt % rel. to entire batch |

* Cr(III) = Cr(III) 2-ethyl-hexanoate (7 wt.-%) in polypropylene glycol 400

TABLE 5

Catalyst combinations tested for the reaction between MAAH and PO

| Ex. | Catalytic system from Table 4 | Color | Comment | MAAH GC area-% | PO GC area-% | Product GC area-% |
|---|---|---|---|---|---|---|
| 15 | 1 | brown | solids precipitated | 0.136 | 1.110 | 91.464 |
| 16 | 2 | grey | solids precipitated | 0.096 | 0.939 | 91.450 |
| 17 | 3 | brown | solids precipitated | 0.104 | 1.197 | 90.395 |
| 18 | 4 | green | solids precipitated | 0.100 | 1.241 | 91.346 |

The results show that the amount of the chromium (III) catalyst in the catalytic system can be varied within abroad range without noticeable change in observed product yields.

Examples 19-23: Reaction Between MAAH and PO in Presence Different Catalyst Amounts A catalyst/co-catalyst mixture, containing different amounts of MgBr$_2$ with Cr(III) salt and TEBAC selected from Table 6 was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for 3 h to 70° C.

After the time had elapsed, the sample was cooled to room temperature and analyzed using GC.

TABLE 6

Catalytic system for the reaction between MAAH and PO in Table 7

| Nr. | | Catalyst/co-catalyst | |
|---|---|---|---|
| 1 | 0.0058 g | MgBr$_2$*6 H$_2$O | 0.10 mol.-% rel. to PO |
|   | 0.0456 g | TEBAC | 1.00 mol.-% rel. to PO |
|   | 0.0318 g | Cr(III) * | 0.75 wt.-% rel. to entire batch |
| 2 | 0.0117 g | MgBr$_2$*6 H$_2$O | 0.20 mol.-% rel. to PO |
|   | 0.0228 g | TEBAC | 0.50 mol.-% rel. to PO |
|   | 0.0318 g | Cr(III) * | 0.75 wt.-% rel. to entire batch |
| 3 | 0.0117 g | MgBr$_2$*6 H$_2$O | 0.20 mol.-% rel. to PO |
|   | 0.0228 g | TEBAC | 0.50 mol.-% rel. to PO |
|   | 0.0212 g | Cr(III) * | 0.50 wt.-% rel. to entire batch |
| 4 | 0.0117 g | MgBr$_2$*6 H$_2$O | 0.20 mol.-% rel. to PO |
|   | 0.0114 g | TEBAC | 0.25 mol.-% rel. to PO |
|   | 0.0212 g | Cr(III) * | 0.50 wt.-% rel. to entire batch |
| 5 | 0.0117 g | MgBr$_2$*6 H$_2$O | 0.20 mol.-% rel. to PO |
|   | 0.0114 g | TEBAC | 0.25 mol.-% rel. to PO |
|   | 0.0106 g | Cr(III) * | 0.25 wt.-% rel. to entire batch |

* Cr(III) = Cr(III) 2-ethyl-hexanoate (7 wt.-%) in polypropylene glycol 400

The composition of the obtained product mixtures is summarized in Table 7.

TABLE 7

Catalyst combinations tested for the reaction between MAAH and PO

| Ex. | Catalytic system from Table 6 | Color | Comment | MAAH GC area-% | PO GC area-% | Product GC area-% |
|---|---|---|---|---|---|---|
| 19 | 1 | brown | | 0.136 | 0.637 | 88.176 |
| 20 | 2 | grey | | 0.096 | 1.007 | 91.955 |
| 21 | 3 | grey | | 0.104 | 1.136 | 89.036 |
| 22 | 4 | grey | | 0.100 | 1.843 | 87.998 |
| 23 | 5 | green | solids precipitated | 8.912 | 4.353 | 75.943 |

All tested catalytic systems allowed preparation of the desired product in good yields.

Examples 24-29: Reaction Between MAAH and PO at 70° C. in Presence of a Catalyst/Co-Catalyst Mixture with Different Reaction Times A catalyst/co-catalyst mixture, containing 0.0117 g MgBr$_2$*6 H$_2$O with 0.0318 g Cr(III) 2-ethylhexanoate (7 wt.-%) in polypropylene glycol 400 and 0.0228 g TEBAC was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for different time (cf. Table 8) to 70° C.

After the time had elapsed, the sample was cooled to room temperature and analyzed using GC.

TABLE 8

Catalyst combinations tested for the reaction between MAAH and PO

| Ex. | Reaction time | Color | Comment | MAAH GC area-% | PO GC area-% | Product GC area-% |
|---|---|---|---|---|---|---|
| 24 | 0.5 h | green |  | 15.841 | 8.145 | 64.961 |
| 25 | 1.0 h | green | solids precipitated | 3.004 | 2.299 | 82.957 |
| 26 | 1.5 h | green |  | 0.137 | 1.117 | 87.432 |
| 27 | 2.0 h | green-gray |  | 0.100 | 1.860 | 88.983 |
| 28 | 2.5 h | dark-green |  | 0.096 | 1.820 | 87.229 |
| 29 | 3.0 h | dark-green |  | 0.116 | 0.679 | 89.018 |

All reactions were substantially complete at 70° C. after 90 min of reaction time.

Examples 30-32: Reaction Between MAAH and PO at 60° C. in Presence of a Catalyst/Co-Catalyst Mixture with Different Reaction Times A catalyst/co-catalyst mixture, containing 0.0117 g MgBr$_2$*6 H$_2$O with 0.0318 g Cr(III) 2-ethylhexanoate (7 wt.-%) in polypropylene glycol 400 and 0.0228 g TEBAC was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for different time (cf. Table 9) to 60° C.

After the time had elapsed, the sample was cooled to room temperature and analyzed using GC.

TABLE 9

Catalyst combinations tested for the reaction between MAAH and PO

| Ex. | Reaction time | Color | MAAH GC area-% | PO GC area-% | Product GC area-% |
|---|---|---|---|---|---|
| 30 | 2.0 h | green | 5.766 | 3.490 | 79.281 |
| 31 | 4.0 h | green | 0.121 | 0.859 | 89.837 |
| 32 | 6.0 h | green | 0.073 | 2.644 | 89.261 |

The reaction rate follows the Arrhenius equation and the reaction can be carried out within a broad temperature range.

Examples 33-37 (Comparative): Reaction Between MAAH and PO in Presence of a Co-Catalyst A catalytic system from Table 10 was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for 3 h to 70° C.

After the time had elapsed, the sample was cooled to room temperature and analyzed using GC.

TABLE 10

Co-catalysts tested for the reaction between MAAH and PO

| Ex. | Catalyst | Amount | Color | MAAH GC area-% | PO GC area-% | Product GC area-% |
|---|---|---|---|---|---|---|
| 33 | Tributyl-phosphine | 0.0817 g (2.0 mol.-%, rel. to PO) | clear, red-brown | 64.989 | 11.327 | 10.322 |
| 34 | Tetrabutylphos-phonium chloride | 0.1180 g (2.0 mol.-%, rel. to PO) | clear, color-less | 39.217 | 16.600 | 31.315 |
| 35 | Triethylamine | 0.0202 g (1.0 mol.-%, rel. to PO) | clear, color-less | 63.161 | 25.711 | 2.651 |
| 36 | Triphenyl-phosphine | 0.0525 g (1.0 mol.-%, rel. to PO) | clear, red-orange | 60.711 | 24.228 | 3.660 |
| 37 | Triethyl-sulfonium bis(trifluoro-methyl-sulfonyl)imide | 0.1598 g (2.0 wt.-% rel. to entire batch) | clear, color-less | 64.691 | 26.435 | 0.027 |

In all tests only minor amounts of the desired product were detected. This indicates that co-catalysts of the present invention (tertiary amines and phosphines) have an insufficiently low catalytic activity in the absence of a first catalyst or a second catalyst.

Examples 38-39: Reaction Between MAAH and PO

Catalytic systems of Table 11 were placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for 3 h to 70° C.

After the time had elapsed, the sample was cooled to room temperature and analyzed using GC.

TABLE 11

Catalytic system for the reaction between MAAH and PO in Table 12

| Nr. | Catalyst/co-catalyst | | |
|---|---|---|---|
| 1 | MgBr$_2$*6 H$_2$O | 0.20 mol.-% | rel. to PO |
|   | tributylphosphine | 2.00 mol.-% | rel. to PO |
|   | Cr(III) * | 0.22 mol.-% | rel. to PO |
| 2 | MgBr$_2$*6 H$_2$O | 0.20 mol.-% | rel. to PO |
|   | tetrabutylphosphonium chloride | 2.00 mol.-% | rel. to PO |
|   | Cr(III) * | 0.22 mol.-% | rel. to PO |

* Cr(III) = Cr(III) 2-ethyl-hexanoate (7 wt.-%) in polypropylene glycol 400

The composition of the obtained product mixtures is summarized in Table 12.

TABLE 12

Catalyst combinations tested for the reaction between MAAH and PO

| Ex. | Catalytic system from Table 11 | Color | MAAH GC area-% | PO GC area-% | Product GC area-% |
|---|---|---|---|---|---|
| 38 | 1 | clear, light brown | 1.7 | 1.3 | 82.0 |
| 39 | 2 | clear, green | 1.1 | 0.6 | 83.0 |

Use of the catalytic system of the present invention allowed preparation of the desired products in good yields.

Examples 40-41 (Comparative): Reaction Between MAAH and THF in Presence of a Co-Catalyst A catalyst/co-catalyst from Table 13 was placed in a 15 ml pressure tube with magnetic stirrer, 3.08 g (0.02 mol) MAAH was added and 1.4422 g (0.02 mol)tetra hydrofurane (THE) were added. The tube was sealed with a Teflon® plug and heated afterwards for 3 h to 70° C.

After the time had elapsed, the sample was cooled to room temperature and analyzed using GC.

TABLE 13

Catalyst tested for the reaction between MAAH and THF

| Ex. | Catalyst/co-catalyst | Amount | Color | MAAH GC area-% | THF GC area-% | Product GC area-% |
|---|---|---|---|---|---|---|
| 40 | TEBAC | 0.0911 g (2.0 mol.-%, rel. to THF) | clear, colorless, with solids | 63.856 | 34.177 | none |
| 41 | $H_2SO_4$, conc. | 0.0144 g (1.0 wt.-%, rel. to THF) | clear, colorless | 63.367 | 33.908 | none |

MAAH did not react with THE under employed conditions and no reaction products were obtained.

Examples 42-47: Reaction Between Various Acid Anhydrides and Different Epoxides

A mixture of 0.0911 g TEBAC (2 mol.-%), $MgBr_2*6H_2O$ (0.2 mol.-%) and Cr(III) 2-ethylhexanoate (7 wt.-%) (0.22 mol.-%) was placed in a 15 ml pressure tube with magnetic stirrer and an epoxide and an acid anhydride selected from Table 13 was added. The tube was sealed with a Teflon® plug and heated afterwards for 3 h to 70° C. After the time had elapsed, the sample was cooled to room temperature and analyzed using GC.

TABLE 14

Epoxide and acid anhydride used in test reactions of Table 13

| Nr. | Starting material | |
|---|---|---|
| 1 | 1.161 g PO = | 0.02 mol |
| 2 | 2.403 g styrene oxide (SO) = | 0.02 mol |
| 3 | 1.963 g cyclohexene oxide (CHO) = | 0.02 mol |
| 4 | 3.0832 g MAAH = | 0.02 mol |
| 5 | 2.5222 g acrylic acid anhydride = | 0.02 mol |
| 6 | 2.0418 g acetic acid anhydride = | 0.02 mol |

TABLE 15 reaction of various epoxides with various anhydrides.

| Ex. | Epoxide and anhydride from Table 13 | Color | Anhydride GC area-% | Epoxide GC area-% | Product GC area-% |
|---|---|---|---|---|---|
| 42 | 1 + 4 | cloudy, green | 1.4 | 0.9 | 83.0 |
| 43 | 2 + 4 | clear, green | 2.29 | 2.29 | 83.0 |
| 44 | 1 + 5 | clear, green | 0.0 | 1.2 | 53 |
| 45 | 1 + 6 | cloudy, green | 7.3 | 8.7 | 68 |
| 46 | 2 + 6 | clear, green | 6.8 | 25.2 | 58 |
| 47 | 3 + 6 | clear, green | 34.4 | 13.6 | 41 |

The performed tests confirm that the process of the present invention is applicable to a broad range of starting materials.

Example 48: Reaction of MAAH with PO on 1 L Scale

Equipment: 1 L reactor equipped with a porcelain stirrer with motor and a Teflon® sleeve, NiCr—Ni thermocouple, reflux cooler, dropping funnel (coolable) with cryostat (−10° C.), thermostat for heating of the reactor.

Chemicals:

| | | | |
|---|---|---|---|
| 770.8 g | MAAH = | 5 mol | |
| 290.4 g | PO = | 5 mol, ratio = 1:1 | |
| 2.92 g | $MgBr_2*6 H_2O$ = | 0.20 mol.-% | rel. to PO |
| 5.69 g | TEBAC = | 0.50 mol.-% | rel. to PO |
| 7.96 g | Cr(III) 2-ethylhexanoate 7 wt.-% in PPG 400 = | 0.75 wt.-% rel. to entire batch | |

Procedure:

The catalysts and co-catalyst were placed in the reactor with MAAH and heated. PO was slowly added at first at 30° C. (exothermic reaction) continued at 40 to 50° C. and finally at 60° C. whereby previously unreacted PO was consumed. Subsequently the temperature was lowered to 55° C. until all remaining PO was added.

The reaction was finally continued at an inner temperature of ca. 70° C. for 2 hours, before the reaction was cooled to RT and analyzed by GC.

The reaction product contained 31 ppm inhibitor and had a purity of 84.7 GC-area-%.

Example 49: Reaction of MAAH with Isobutenoxide

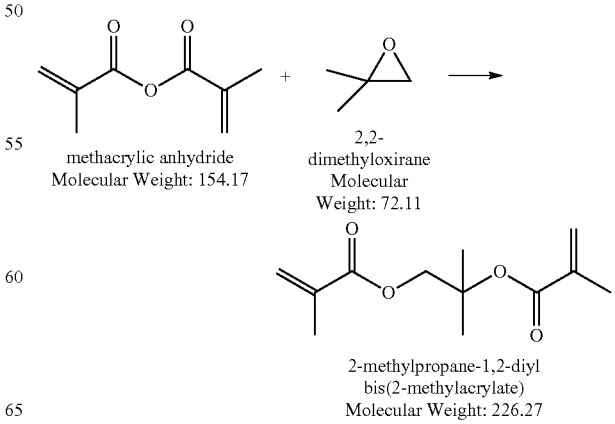

methacrylic anhydride
Molecular Weight: 154.17

2,2-dimethyloxirane
Molecular Weight: 72.11

2-methylpropane-1,2-diyl bis(2-methylacrylate)
Molecular Weight: 226.27

Equipment: 1 L 4-necked flask with a porcelain stirrer with motor and a Teflon® sleeve, thermometer, reflux condenser.

Chemicals:

| Isobutenoxide | 216.33 g = | 3.00 mol |
|---|---|---|
| MAAH | 462.48 g = | 3.00 mol |
| Phenothazine | 1.51 g = | 2000 ppm |
| MgBr$_2$*6 H$_2$O | 1.75 g = | 0.20 mol % |
| TEBAC | 3.42 g = | 0.50 mol % |
| Cr(III) * | 4.40 g = | 0.22 mol % |

Procedure:

The catalysts and co-catalyst were placed in the flask with MAAH and heated. The epoxide was slowly added at 80° C. The reaction was finally continued at an inner temperature of ca. 80° C. for 15 hours, before the reaction was cooled to RT and analyzed by GC.

The reaction product had a purity of 56.3 GC-area-%.

Example 50 (Comparative): Reaction of MAAH with Isobutenoxide

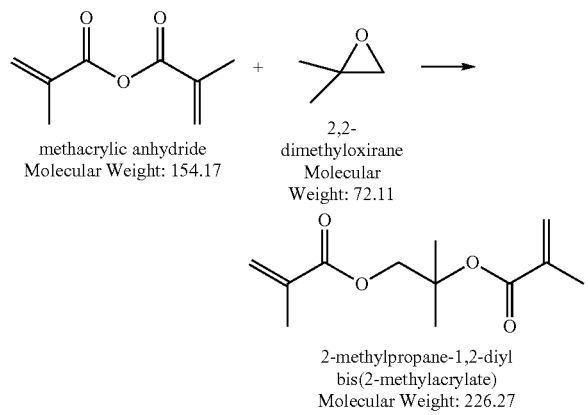

methacrylic anhydride
Molecular Weight: 154.17

2,2-dimethyloxirane
Molecular Weight: 72.11

2-methylpropane-1,2-diyl bis(2-methylacrylate)
Molecular Weight: 226.27

Equipment: 500 mL 4-necked flask with a porcelain stirrer with motor and Teflon sleeve, thermometer, reflux condenser.

Chemicals:

| Isobutenoxide | 108.17 g = | 1.50 mol |
|---|---|---|
| MAAH | 231.24 g = | 1.50 mol |
| Phenothazine | 0.76 g = | 2000 ppm |
| DMAP | 3.67 g = | 2.00 mol % |

Procedure:

The co-catalyst was placed in the flask with MAAH and heated. The epoxide was slowly added to the reaction mixture at 80° C.

The reaction was finally continued at an inner temperature of ca. 80° C. for 5 hours, before the reaction mixture was cooled to RT and analyzed by GC.

No desired product was detected.

Example 51: Reaction of MAAH with PO on 2 L Scale

Equipment: 2 L autoclave with an inner glass beaker (1.6 L), autoclave rack, stirring motor, oil bath, glass piston pump, coolable dropping funnel, cryostat (5° C.)

Chemicals:

| 925 g | MAAH = | 6 mol | |
|---|---|---|---|
| 348.5 g | PO = | 6 mol | ratio = 1:1 |
| 3.51 g | MgBr$_2$*6 H$_2$O = | 0.20 mol.-% rel. to PO | |
| 6.83 g | TEBAC = | 0.50 mol.-% rel. to PO | |
| 9.55 g | Cr(III) 2-ethylhexanoate 7 wt.-% in PPG 400 = | 0.75 wt.-% rel. to entire batch | |

Procedure:

The catalysts/co-catalyst (MgBr$_2$, TEBAC and Cr(III)) were fed with MAAH into the glass beaker of the autoclave. The autoclave was sealed and heated to 60° C. Then PO (precooled to 5° C. in a dropping funnel) was fed with a glass piston pump into the reactor. The resulting pressure was kept below 1.5 bar and the temperature around 70° C.

After the end of dosing, stirring was continued at 70° C. for 2 hours. The oil bath is then removed and the autoclave was ventilated.

Temperature Control:

The oil bath was removed at an internal temperature of 60° C. Reaction temperature of 70° C. was controlled by dosing without medium. Over temperature was counter-cooled with water bath, in case of insufficient temperature, heating with oil bath.

Protocol:

| local Time | Bath-Temp [° C.] | Inner-Temp. [° C.] | Pressure [bar] | remark |
|---|---|---|---|---|
| 11:45 | 23 | 22 | — | heating |
| 12:15 | 64 | 43 | 0 | data loggers starts |
| 13:10 | 70 | 62 | 0.1 | heating removed, pump 150 ml/h PO |
| 13:25 | 34 | 66 | 0.5 | pump 200 ml/h PO |
| 13:40 | 33 | 67 | 0.7 | — |
| 13:55 | 27 | 75 | 0.9 | cooling, pump stoped |
| 14:15 | 14 | 74 | 0.5 | cooling removed, pump 200 ml/h PO |
| 15:13 | 25 | 63 | 1 | pump 150 ml/h PO |
| 15:22 | | | | 1 min. cooling, pump 200 ml/h PO |
| 15:47 | 27 | 64 | 1.1 | — |
| 16:08 | 15 | 70 | 1.4 | 1 minute cooling |
| 16:22 | 27 | 66 | 1.3 | End of dosing, sample A |
| 16:38 | 43 | 65 | 1.1 | heat |
| 16:56 | 65 | 70 | 1.2 | Heating removed |
| 17:23 | 33 | 69 | 0.8 | Sample B |
| 17:37 | 62 | 66 | 0.8 | heat |
| 18:20 | 70 | 62 | — | Sample C, ventilated & cool down |

Result:

1251.3 g of a clear dark green liquid which fills the container to ¾ was obtained.

| Sample | | Epoxide GC area-% | MAAH GC area-% | Product GC area-% |
|---|---|---|---|---|
| Sample A | End of dosing | 1.800 | 18.750 | 68.353 |
| Sample B | 1 h post-reaction | 0.260 | 1.277 | 87.678 |
| Sample C | 2 h post-reaction | 0.150 | 0.197 | 89.010 |

An excellent reaction conversion upon formation of the desired product was observed.

Example 52: Reaction of MAAH with PO on 24 L Scale

Equipment:

24 L autoclave with double jacket reactor, temperature control unit (single), agitator motor, scale, glass piston lifting pump, Paravisc agitator Chemicals

| 9.25 kg | MAAH = | 60 mol |
|---|---|---|
| 3.48 kg | PO = | 60 mol, ratio = 1:1 |
| 35.1 g | MgBr$_2$*6 H$_2$O = | 0.20 mol.-% rel. to PO |
| 68.3 g | TEBAC = | 0.50 mol.-% rel. to PO |
| 95.5 g | Cr(III) 2-ethylhexanoate 7 wt.-% in PPG 400 = | 0.75 wt.-% rel. to entire batch |

Procedure:

The catalytic system (MgBr$_2$, TEBAC and Cr(III)) was placed into the autoclave and MAAH was fed with a pump. (The solid catalysts must be placed in the open autoclave, as they do not dissolve and therefore cannot be fed via pipes).

The autoclave was sealed and heated to 60° C. Then PO was fed with a glass piston pump into the reactor. The resulting pressure was kept below 1.5 bar (no pressure build up was noticed) and the temperature was between 65 and 75° C. After the end of dosing, stirring was continued at 70° C. for 2 hours. The autoclave was then cooled to RT and finally ventilated.

Temperature Control:

The oil bath was removed at an internal temperature of 60° C. Reaction temperature of 70° C. was controlled by dosing without applying cooling or heating medium.

Protocol:

| Reaction Time | Oil @-entry [° C.] | Oil @-exit [° C.] | Inner-Temp. [° C.] | Pressure [bar] | Pump | remark |
|---|---|---|---|---|---|---|
| 00:00 | 15 | 15 | 17 | 0/— | — | heating to 65° C. |
| 00:12 | 64 | 61 | 28 | 0/— | — | heating to 75° C. |
| 00:50 | 68 | 65 | 59 | 0/0 | on | heating to 60° C. |
| 01:00 | 58 | 57 | 59 | 0/0 | ~12.5 g/min | heating to 63° C., addition of 126 g PO |
| 01:18 | 61 | 60 | 60 | 0/0 | ~12.5 g/min | addition of 348 g PO ~1/10 of total amount |
| 01:42 | 61 | 61 | 65 | 0/0 | ~12.5 g/min. | heating stopped, cooling |
| 03:00 | 54 | 54 | 69 | 0/0 | ~12.5 g/min. | — |
| 04:00 | 51 | 52 | 70 | 0/0 | ~12.5 g/min. | — |
| 05:00 | 53 | 54 | 70 | 0/0 | ~12.5 g/min. | — |
| 05:20 | 53 | 54 | 70 | 0/0 | off | end of dosing |
| 05:25 | 53 | 54 | 69 | 0/— | — | heating |
| 07:00 | 70 | 69 | 69 | 0/— | — | — |
| 07:40 | 70 | 69 | 69 | 0/— | — | cooling |
| 08:00 | 27 | 33 | 49 | 0/— | — | — |
| 08:20 | 20 | 23 | 32 | 0/— | — | Ventilated, switched off |
| 09:00 | 15 | 15 | 17 | 0/— | — | heating to 65° C. |
| 09:12 | 64 | 61 | 28 | 0/— | — | heating to 75° C. |

13.6 kg of a liquid with suspended particles was obtained. Product yield: 93.30% (GC area-%), Remaining Inhibitor=47 ppm

Example 53: Reaction of MAAH with EO on 1 L Scale

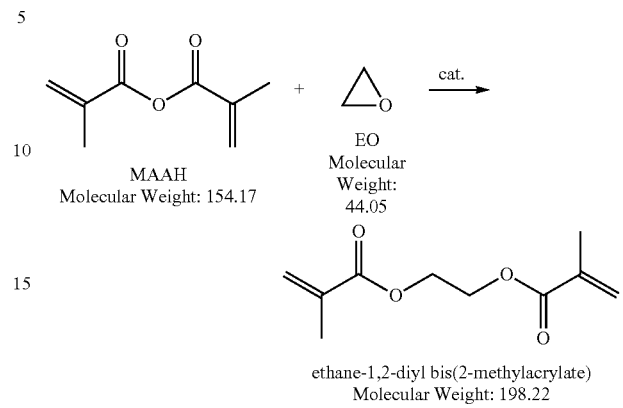

ethane-1,2-diyl bis(2-methylacrylate)
Molecular Weight: 198.22

Equipment: 5 L-pressure reactor with oil circulation, temperature regulator, anchor stirrer, manhole, storage tank for epoxy on scale, acid scrubber (H$_3$PO$_4$)

Chemicals:

| 308.32 g | MAAH = | 2.00 mol | |
|---|---|---|---|
| 88.10 g | EO = | 2.00 mol | ratio = 1:1 |
| 1.1688 g | MgBr$_2$*6 H$_2$O = | 0.20 mol.-% | rel. to EO |
| 2.2777 g | TEBAC = | 0.50 mol.-% | rel. to EO |
| 3.1836 g | Cr(III) 2-ethylhexanoate in PPG 400 [~7.8% Cr] = | 0.39 mol.-% | rel. to EO |
| 0.3964 g | phenothiazine = | 1000 ppm rel. to MAAH | |

Procedure:

The catalytic system (MgBr$_2$, TEBAC and Cr(III)) was placed into the pressure reactor and MAAH was fed with a pump. The pressure reactor was sealed and flushed three times with nitrogen. Subsequently, the pressure reactor was evacuated (0.1 bar) and filled with nitrogen to atmospheric pressure. The pressure reactor was heated to 60° C. inner temperature. Then EO (16 g) was fed into the pressure reactor. The resulting pressure was kept below 1.5 bar and reached 0.8 bar overpressure after addition of 29 g EO were fed.

The temperature was increased first to 65° C. and then to 70° C. At this temperature the pressure dropped and the overpressure was kept constant at about 0.5 bar by adding portions of EO. At the end of dosing, stirring was continued at 75° C. for 2 hours. Since the overpressure (0.2 bar) did not completely disappeared, the temperature was elevated to 80° C. for 30 min.

The pressure reactor was then cooled to RT and finally ventilated.

Protocol:

| Time hh:mm | Reaction-temp. ° C. | Oil-temp. ° C. | Over-pressure bar | Remarks |
|---|---|---|---|---|
| | RT | — | 0/-0.9 | Reactor rinsed 3 times with nitrogen. 1 time evacuated and relaxed to standard pressure with nitrogen |
| 00:00 | 24 | — | 0 | heating to 60° C. |
| 00:05 | 61 | 65 | 0.1 | dosage of 16 g EO |
| 00:15 | 60 | 64 | 0.3 | dosage of 29 g EO |

-continued

| Time hh:mm | Reaction-temp. °C. | Oil-temp. °C. | Over-pressure bar | Remarks |
|---|---|---|---|---|
| 00:20 | 60 | 62 | 0.8 | |
| 00:35 | 60 | 62 | 0.8 | heating to 65° C. |
| 00:52 | 65 | 69 | 0.8 | heating to 70° C. |
| 00:55 | 73 | 78 | 0.8 | |
| 01:02 | 70 | 73 | 0.75 | |
| 01:10 | 70 | 72 | 0.6 | |
| 01:20 | 70 | 72 | 0.45 | dosage of 20 g EO |
| 01:45 | 70 | 71 | 0.55 | |
| 01:50 | 70 | 71 | 0.5 | dosage of 20 g EO |
| 02:05 | 70 | 72 | 0.75 | heating to 75° C. |
| 02:10 | 77 | 79 | 0.7 | |
| 02:15 | 75 | 77 | 0.6 | |
| 02:45 | 75 | 79 | 0.2 | |
| 03:48 | 75 | 78 | 0.2 | heating to 80° C. |
| 03:53 | 80 | 84 | 0.2 | |
| 04:07 | 80 | 84 | 0.2 | cooling to 40° C. |
| 04:20 | 50 | — | 0.1 | |
| 04:35 | 40 | — | −0.9 | relaxation with nitrogen |

385 g of a dark green liquid without solids was obtained. Purity of the isolated ethylene glycol dimethacrylate was 89.71% (GC)

Example 54: Reaction of MAAH with EO on 2 L Scale

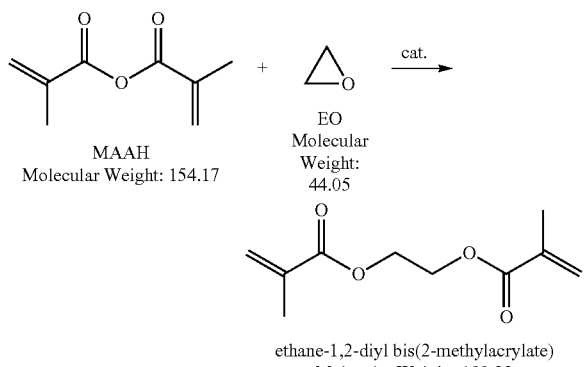

MAAH
Molecular Weight: 154.17

EO
Molecular Weight: 44.05 ethane-1,2-diyl bis(2-methylacrylate)
Molecular Weight: 198.22

Equipment: 5 L-pressure reactor with oil circulation, Juchheim temperature regulator, anchor stirrer, manhole, storage tank for epoxy on scale, acid scrubber ($H_3PO_4$)
Chemicals:

| 1.23 kg | MAAH = | 8.00 mol | |
|---|---|---|---|
| 352.4 g | EO = | 8.00 mol | ratio = 1:1 |
| 4.68 g | $MgBr_2$*6 $H_2O$ = | 0.20 mol.-% | rel. to EO |
| 9.11 g | TEBAC = | 0.50 mol.-% | rel. to EO |
| 11.73 g | Cr(III) 2-ethylhexanoate in PPG 400 [~7.8% Cr] = | 0.39 mol.-% | rel. to EO |
| 1.59 g | phenothiazine = | 1000 ppm | rel. to MAAH |

Procedure:
The catalytic system ($MgBr_2$, TEBAC and Cr(III)) were placed into the pressure reactor and MAAH was fed with a pump. The pressure reactor was sealed and flushed three times with nitrogen. The pressure reactor was evacuated (0.1 bar) and filled with nitrogen to atmospheric pressure and heated to 70° C.

Then EO was fed (~6 g/min) into the pressure reactor. The resulting overpressure was kept below 1 bar. At the end of dosing, stirring was continued at 75° C. for about 2 hours. The pressure reactor was then cooled to RT and finally ventilated.

Protocol:

| Time hh:mm | Reaction temp. °C. | Oil temp. °C. | Over-pressure bar | Remarks |
|---|---|---|---|---|
| 00:00 | RT | — | 0/−0.9 | reactor was rinsed 3 times with nitrogen, evacuated 1 time and expanded to standard pressure with nitrogen. Heating to 70°C. |
| 00:09 | 71 | 75 | 0.2 | dosing approx. 6 g/min EO up to max. 1 bar overpressure |
| 00:19 | 70 | 75 | 0.5 | dosing 60 g EO |
| 00:29 | 70 | 70 | 0.8 | dosing 100 g EO |
| 00:39 | 70 | 70 | 1 | dosing 145 g EO |
| 00:49 | 70 | 68 | 1.05 | dosing 183 g EO |
| 00:59 | 70 | 67 | 1.05 | dosing 218 g EO |
| 01:09 | 70 | 66 | 0.95 | dosing 253 g EO |
| 01:19 | 70 | 66 | 0.85 | dosing 289 g EO |
| 01:29 | 70 | 66 | 0.8 | dosing 331 g EO |
| 01:38 | 70 | 67 | 0.8 | dosing 361 g EO |
| 01:49 | 70 | 70 | 0.5 | |
| 01:59 | 70 | 71 | 0.35 | |
| 02:09 | 70 | 72 | 0.3 | |
| 02:19 | 70 | 72 | 0.25 | |
| 02:29 | 70 | 72 | 0.25 | |
| 02:39 | 70 | 73 | 0.25 | |
| 02:49 | 70 | 73 | 0.225 | |
| 02:59 | 70 | 73 | 0.225 | |
| 03:59 | 70 | 73 | 0.2 | cooling to 40° C. |
| 04:09 | 51 | — | −0.9 | deodorization |
| 04:24 | 40 | — | 0 | pressure relief to normal pressure under nitrogen |

1601 g of a dark green liquid with solid was obtained. Purity of the obtained ethylene glycol dimethacrylate was 93.60% (GO).

Example 55 (Comparative): Reaction of MAAH with Hexene Oxide in the Presence of an Erbium(III) Catalyst The protocol follows the literature procedure described in R. Dalpozoet a (ARKIVOC (Gainesville, Fla., United States) (2006), (6), 67-73.

Chemicals:

| 1.00 g | hexene oxide = | 0.01 mol |
|---|---|---|
| 3.08 g | MAAH = | 0.02 mol |
| 6.1 mg | erbium (III) triflate = | 0.10 mol.-% |

Procedure:
All chemicals were filled into a 15 ml pressure tube with magnetic stirrer. The tube was sealed with a Teflon® plug and stirred for 1 h at room temperature. After the time had elapsed, the sample was analyzed using GC.

No product formation was observed.

Example 56 (Comparative) Reaction of MAAH with PO in the Presence of an Erbium(II) Catalyst The protocol follows the literature procedure described in R. Dalpozo et al. (ARKIVOC (Gainesville, Fla., United States) (2006), (6), 67-73.

Chemicals:

| 1.16 g | PO = | 0.02 mol |
|---|---|---|
| 3.08 g | MAAH = | 0.02 mol |
| 12.3 mg | erbium (III) triflate = | 0.10 mol.-% |

Procedure:
All chemicals were filled into a 15 ml pressure tube with magnetic stirrer. The tube was sealed with a Teflon® plug and stirred for 1 h at room temperature. After the time had elapsed, the sample was analyzed using GC.
No product formation was observed.

Example 57 (Comparative) Reaction of MAAH with PO in the Presence of an Erbium(III) Catalyst The protocol follows the literature procedure described in R. Dalpozo et al. (ARKIVOC (Gainesville, Fla., United States) (2006), (6), 67-73.
Chemicals:

| 1.16 g | PO = | 0.02 mol |
|---|---|---|
| 3.08 g | MAAH = | 0.02 mol |
| 12.3 mg | erbium (III) triflate = | 0.10 mol.-% |

Procedure:
All chemicals were filled into a 15 ml pressure tube with magnetic stirrer. The tube was sealed with a Teflon® plug and stirred for 1 h at 80° C. After the time had elapsed, the sample was cooled to room temperature and analyzed using GC.
Only 0.6 GC-area-% product could be obtained Example 58 (Comparative): Reaction of Acetic Anhydride with Hexene Oxide in the Presence of Tributylphophine The protocol follows the literature procedure described in Ren-Hua et al. (Tetrahedron Letters (2003), 44(23).
Chemicals:

| 2.00 g | 1-hexene oxide = | 0.02 mol |
|---|---|---|
| 2.04 g | acetic anhydride = | 0.02 mol |
| 0.41 g | tributylphosphine = | 10 mol.-%. |

Procedure:
All chemicals were filled into a 15 ml pressure tube equipped with a magnetic stirrer. The tube was sealed with a Teflon® plug and stirred for 24 h at 110° C. After the time had elapsed, the sample was cooled to room temperature and analyzed using GC.
83.01 GC-area-% product could be obtained.

Example 59 (Comparative): Reaction of MAAH with Hexene Oxide in the Presence of Tributylphophine The protocol follows the literature procedure described in Ren-Hua et al. (Tetrahedron Letters (2003), 44(23).
Chemicals:

| 2.00 g | 1-hexene oxide = | 0.02 mol |
|---|---|---|
| 3.08 g | MAAH = | 0.02 mol |
| 408 mg | tributylphosphine = | 10 mol.-%. |

Procedure:
All chemicals were filled into a 15 ml pressure tube with magnetic stirrer. The tube was sealed with a Teflon® plug and stirred for 24 h at 110° C. After the time had elapsed, the sample was polymerized.
No desired product could be obtained.

Example 60 (Comparative): Reaction of MAAH with PO in the Presence of Zeolith CP 814E at Room Temperature The protocol follows the literature procedure described in P. Ramesh et al., Synthetic Communications (2001), 31(17), 2599-2604.
Chemicals:

| 1.16 g | PO = | 0.02 mol |
|---|---|---|
| 3.08 g | MAAH = | 0.02 mol |
| 690 mg | Zeolith CP 814E = | 59.4 wt.-% |

Procedure:
All chemicals were filled into a 15 ml pressure tube with magnetic stirrer. The tube was sealed with a Teflon® plug and stirred for 9.5 h at room temperature. After the time had elapsed, the sample was cooled to room temperature and analyzed using GC.
No product could be obtained.

Comparative Example 61: Reaction of MAAH with PO in the Presence of Zeolith CP 814E at 80° C.

The protocol follows the literature procedure described in P. Ramesh et al., Synthetic Communications (2001), 31(17), 2599-2604.
Chemicals:

| 1.16 g | PO = | 0.02 mol |
|---|---|---|
| 3.08 g | MAAH = | 0.02 mol |
| 690 mg | Zeolith CP 814E = | 59.4 wt.-% |

Procedure:
All chemicals were filled into a 15 ml pressure tube with magnetic stirrer. The tube was sealed with a Teflon® plug and stirred for 9.5 h at 80° C. After the time had elapsed, the sample was cooled to room temperature and analyzed using GC.
Only 1.08 GC-area-% product was formed.

Example 62 (Comparative): Reaction of MAAH and SO in the Presence of $Na_2HPO_4$ The protocol follows the literature procedure described in M. Gilanizadeh et al., Journal of Chemical Research (2016), 40(5), 296-298.
Chemicals:

| 0.60 g | Styrene oxide (SO) = | 5 mmol |
|---|---|---|
| 8.09 g | MAAH = | 53 mmol |
| 895 mg | $Na_2HPO_4$*10 $H_2O$ = | 50 mol.-% rel. to SO |

Procedure:
All chemicals were filled into a 15 ml pressure tube with magnetic stirrer. The tube was sealed with a Teflon® plug and stirred for 2 h at 110° C. After the time had elapsed, the sample was polymerized
No product could be obtained.

Example 63 (Comparative): Reaction of MAAH and SO in the Presence of NaHSO$_4$ The protocol follows the literature procedure described in M. Gilanizadeh et al., Journal of Chemical Research (2016), 40(5), 296-298.

Chemicals:

| 0.60 g | SO = | 5 mmol |
|---|---|---|
| 8.09 g | MAAH = | 53 mmol |
| 345 mg | NaHSO$_4$*H$_2$O = | 50 mol.-%. rel. to SO |

Procedure:

All chemicals were filled into a 15 ml pressure tube with magnetic stirrer. The tube was sealed with a Teflon® plug and stirred for 2 h at 110° C. After the time had elapsed, the sample was polymerized.

No product could be obtained.

Example 64 (Comparative): Reaction of Acetic Anhydride and PO in the Presence of Tetrabutyl Ammonium Acetate The protocol follows the literature procedure described in Md. A. Rahman et al., *J. Am. Chem. Soc.* 1985, 107, 5576-5578.

Chemicals:

| 1.16 g | PO = | 0.02 mol |
|---|---|---|
| 2.04 g | acetic anhydride = | 0.02 mol |
| 302 mg | tetrabutyl ammonium acetate = | 5 mol.-%. |

Procedure:

All chemicals were filled into a 15 ml pressure tube with magnetic stirrer. The tube was sealed with a Teflon® plug and stirred for 6 h at 80° C. After the time had elapsed, the sample was cooled to room temperature and analyzed using GC.

77.27 GC-area-% product was formed at nearly complete conversion.

Example 65 (Comparative): Reaction of MAAH and PO in the Presence of Tetrabutyl Ammonium Acetate The protocol follows the literature procedure described in Md. A. Rahman et al., *J. Am. Chem. Soc.* 1985, 107, 5576-5578.

Chemicals:

| 1.16 g | PO = | 0.02 mol |
|---|---|---|
| 2.04 g | MAAH = | 0.02 mol |
| 302 mg | tetrabutyl ammonium acetate = | 5 mol.-%. |

Procedure:

All chemicals were filled into a 15 ml pressure tube with magnetic stirrer. The tube was sealed with a Teflon® plug and stirred for 3 h at 70° C. After the time had elapsed, the sample was cooled to room temperature and analyzed using GC.

36 GC-area-% product was formed.

Example 66: Reaction of MAAH and PO in the Presence of Tetrabutyl Ammonium Acetate in Combination with Magnesium Bromide and a Chromium (III) Catalyst Chemicals:

| 1.16 g | PO = | 0.02 mol |
|---|---|---|
| 2.04 g | MAAH = | 0.02 mol |
| 302 mg | tetrabutyl ammonium acetate = | 5 mol.-%. |
| 0.0117 g | MgBr$_2$*6 H$_2$O = | 0.2 mol.-% |
| 0.0318 g | Cr(III) 2-ethyl-hexanoate (7 wt.-%) in PPG 400 = | 0.22 mol.-% |

Procedure:

All chemicals were filled into a 15 ml pressure tube with magnetic stirrer. The tube was sealed with a Teflon® plug and stirred for 3 h at 70° C. After the time had elapsed, the sample was cooled to room temperature and analyzed using GC.

68 GC-area-% product was formed.

Example 67 (Comparative): Reaction of Acetic Anhydride with PO in the Presence of Triethylamine The protocol follows the literature procedure described in U.S. Pat. No. 5,623,086.

Chemicals:

| 0.58 g | PO = | 0.01 mol |
|---|---|---|
| 2.04 g | acetic anhydride = | 0.02 mol |
| 36.4 mg | triethylamine = | 3.60 mol.-% rel. to PO |

Procedure:

All chemicals were filled into a 15 ml pressure tube with magnetic stirrer. The tube was sealed with a Teflon® plug and stirred for 4 h at 120° C. After the time had elapsed, the sample was cooled to room temperature and analyzed using GC.

67.16 GC-area-% product was obtained.

Example 68 (Comparative): Reaction of MAAH with PO in the Presence of Triethylamine at 120° C.

The protocol follows the literature procedure described in U.S. Pat. No. 5,623,086.

Chemicals:

| 0.58 g | PO = | 0.01 mol |
|---|---|---|
| 3.08 g | MAAH = | 0.02 mol |
| 36.4 mg | triethylamine = | 3.60 mol.-% rel. to PO |

Procedure:

All chemicals were filled into a 15 ml pressure tube with magnetic stirrer. The tube was sealed with a Teflon® plug and stirred for 4 h at 120° C. After the time had elapsed, the sample was polymerized.

No product could be obtained.

Example 69 (Comparative): Reaction of MAAH with PO in the Presence of Triethylamine at 80° C.

The protocol follows the literature procedure described in U.S. Pat. No. 5,623,086.

Chemicals:

| 0.58 g | PO = | 0.01 mol |
|---|---|---|
| 3.08 g | MAAH = | 0.02 mol |
| 36.4 mg | triethylamine = | 3.60 mol.-% rel. to PO |

Procedure:

All chemicals were filled into a 15 ml pressure tube with magnetic stirrer. The tube was sealed with a Teflon® plug and stirred for 3 h at 70° C. After the time had elapsed, the sample was polymerized.

6% product could be obtained.

Example 70 (Comparative): Reaction of Acetic Anhydride with SO in the Presence of Tetrabutyl Ammonium Chloride The protocol follows the literature procedure described in G. Fogassy et al., *Catalysis Communications* 2009, No. 10, 557-560.

Chemicals:

| 2.40 g | SO = | 0.02 mol |
|---|---|---|
| 2.04 g | acetic anhydride = | 0.02 mol |
| 278 mg | tetrabutyl ammonium chloride = | 5 mol.-%. |

Procedure:

All chemicals were filled into a 15 ml pressure tube with magnetic stirrer. The tube was sealed with a Teflon® plug and stirred for 3 h at 110° C. After the time had elapsed, the sample was cooled to room temperature and analyzed using GC.

87.42 GC-area-% product could be obtained.

Example 71 (Comparative): Reaction of MAAH with SO in the Presence of Tetrabutyl Ammonium Chloride The protocol follows the literature procedure described in G. Fogassy et al., *Catalysis Communications* 2009, No. 10, 557-560.

Chemicals:

| 2.40 g | SO = | 0.02 mol |
|---|---|---|
| 3.08 g | MAAH = | 0.02 mol |
| 278 mg | tetrabutyl ammonium chloride = | 5 mol.-%. |

Procedure:

All chemicals were filled into a 15 ml pressure tube with magnetic stirrer. The tube was sealed with a Teflon® plug and stirred for 3 h at 110° C. After the time had elapsed, the sample was polymerized.

No product could be obtained.

Example 72 (Comparative): Reaction of MAAH with PO in the Presence of Tetrabutyl Ammonium Chloride The protocol follows the literature procedure described in G. Fogassy et al., *Catalysis Communications* 2009, No. 10, 557-560.

Chemicals:

| 1.16 g | PO = | 0.02 mol |
|---|---|---|
| 3.08 g | MAAH = | 0.02 mol |
| 278 mg | tetrabutyl ammonium chloride = | 5 mol.-%. |

Procedure:

All chemicals were filled into a 15 ml pressure tube with magnetic stirrer. The tube was sealed with a Teflon® plug and stirred for 3 h at 110° C. After the time had elapsed, the sample was polymerized.

No product could be obtained.

Example 73 (Comparative): Reaction of Acetic Anhydride with PO in the Presence of Pyridine The protocol follows the literature procedure described in V. F. Shveets et al. (Kinet. Katal. 1975, 16, 785.

Chemicals:

| 1.16 g | PO = | 0.02 mol |
|---|---|---|
| 2.04 g | acetic anhydride = | 0.02 mol |
| 791 mg | pyridine = | 5 mol %. |

Procedure:

All chemicals were filled into a 15 ml pressure tube with magnetic stirrer. The tube is sealed with a Teflon® plug and stirred for 6 h at 105° C. After the time had elapsed, the sample was cooled to room temperature and analyzed using GC.

54.22 GC-Area % product could be obtained.

Example 74 (Comparative): Reaction of MAAH with PO in the Presence of Pyridine The protocol follows the literature procedure described in V. F. Shveets et al. (Kinet. Katal. 1975, 16, 785.

Chemicals:

| 1.16 g | PO = | 0.02 mol |
|---|---|---|
| 3.08 g | MAAH = | 0.02 mol |
| 791 mg | pyridine = | 5 mol %. |

Procedure:

All chemicals were filled into a 15 ml pressure tube with magnetic stirrer. The tube is sealed with a Teflon® plug and stirred for 3 h at 70° C. After the time had elapsed, the sample was cooled to room temperature and analyzed using GC.

Only 8 GC-Area % product could be obtained.

Example 75 (Comparative): Reaction of Acetic Anhydride with PO in the Presence of Disodium Phthalate The protocol follows the literature procedure described in E. Schwenk et al., Makromol. Chem. 1962, 51, 53-69.

Chemicals:

| | | |
|---|---|---|
| 1.16 g | PO = | 0.02 mol |
| 2.04 g | acetic anhydride = | 0.02 mol |
| 210 mg | disodium phthalate = | 5 mol.-%. |

Procedure:
All chemicals were filled into a 15 ml pressure tube with magnetic stirrer. The tube was sealed with a Teflon® plug and stirred for 6 h at 130° C. After the time had elapsed, the sample was cooled to room temperature and analyzed using GC.
47.63 GC-area-% product could be obtained.

Example 76 (Comparative): Reaction of MAAH with PO in the Presence of Disodium Phthalate The protocol follows the literature procedure described in E. Schwenk et al., Makromol. Chem. 1962, 51, 53-69.
Chemicals:

| | | |
|---|---|---|
| 1.16 g | PO = | 0.02 mol |
| 3.08 g | MAAH = | 0.02 mol |
| 210 mg | disodium phthalate = | 5 mol.-%. |

Procedure:
All chemicals were filled into a 15 ml pressure tube with magnetic stirrer. The tube was sealed with a Teflon® plug and stirred for 6 h at 130° C. After the time had elapsed, the sample was polymerized.
No product could be obtained.

Example 77 (Comparative): Reaction of Acetic Anhydride with Cyclohexene Oxide in the Presence of Tetrabutylammonium Chloride The protocol follows the literature procedure described in T. Yoshino, J. Chem. Soc., Perkin Trans. 1, 1977, 1266-1272.
Chemicals:

| | | |
|---|---|---|
| 1.96 g | cyclohexene oxide = | 0.02 mol |
| 2.24 g | acetic anhydride = | 0.022 mol |
| 1.00 g | tetrabutyl ammonium chloride = | 18 mol.-%. |

Procedure:
All chemicals were filled into a 15 ml pressure tube with magnetic stirrer. The tube was sealed with a Teflon® plug and stirred for 15 min at 130° C. After the time had elapsed, the sample was cooled to room temperature and analyzed using GC.
44.89 GC-area-% product could be obtained.

Example 78 (Comparative): Reaction of MAAH with Cyclohexene Oxide in the Presence of Tetrabutylammonium Chloride The protocol follows the literature procedure described in T. Yoshino, J. Chem. Soc., Perkin Trans. 1, 1977, 1266-1272.
Chemicals:

| | | |
|---|---|---|
| 1.96 g | cyclohexene oxide = | 0.02 mol |
| 3.39 g | MAAH = | 0.022 mol |
| 1.00 g | tetrabutyl ammonium chloride = | 18 mol.-%. |

Procedure:
All chemicals were filled into a 15 ml pressure tube with magnetic stirrer. The tube was sealed with a Teflon® plug and stirred for 15 min at 130° C. After the time had elapsed, the sample was polymerized:
No product could be obtained.

Examples 79-81: Reaction Between MAAH and PO in Presence of Various Chromium (III) Catalysts A catalyst/co-catalyst mixture, containing different amounts of $MgBr_2$ with a Cr(III) salt and TEBAC selected from Table 4 was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for 3 h to 70° C.

After the time had elapsed, the sample was cooled to room temperature and analyzed using GC.

TABLE 16

Catalytic systems for the reaction between MAAH and PO in Table 16

| Nr. | Catalyst / co-catalyst | | | |
|---|---|---|---|---|
| 1 | 0.0058 g | $MgBr_2$*6 H2O | 0.1 mol.-% | rel. to PO |
| | 0.0911 g | TEBAC | 2 mol.-% | rel. to PO |
| | 0.0023 g | Cr(III) Perchlorate | 0.25 mol.-% | rel. to PO |
| 2 | 0.0058 g | $MgBr_2$*6 $H_2O$ | 0.1 mol.-% | rel. to PO |
| | 0.0911 g | TEBAC | 2 mol.-% | rel. to PO |
| | 0.0212 g | Cr(III) Acetylacetonate | 0.25 mol.-% | rel. to PO |
| 3 | 0.0058 g | $MgBr_2$*6 $H_2O$ | 0.1 mol.-% | rel. to PO |
| | 0.0456 g | TEBAC | 2 mol.-% | rel. to PO |
| | 0.0637 g | Cr(III) chloride × $(THF)_3$ | 0.25 mol.-% | rel. to PO |

TABLE 17

Catalyst combinations tested for the reaction between MAAH and PO

| Ex. | Catalytic system from Table 4 | Comment | MAAH GC area-% | PO GC area-% | Product GC area-% |
|---|---|---|---|---|---|
| 79 | 1 | | 0.176 | 1.710 | 89.365 |
| 80 | 2 | | 0.323 | 0.939 | 90.468 |
| 81 | 3 | | 0.957 | 1.541 | 88.667 |

The results show that the species of chromium (III) catalyst in the catalytic system can be varied within a broad range without noticeable change in observed product yields.

Examples 82-86: Reaction Between MAAH and PO in Presence of Different Rare Earth Triflates A catalyst/co-catalyst mixture, containing different rare earth triflates with Cr(III) 2-ethyl-hexanoate (7 wt.-%) in polypropylene glycol 400 and TEBAC selected from Table 4 was placed in a 15 ml pressure tube with magnetic stirrer, 3.08 g (0.02 mol) MAAH was added and 1.16 g (0.02 mol) PO were carefully added dropwise. The tube was sealed with a Teflon® plug and heated afterwards for 3 h to 70° C.

After the time had elapsed, the sample was cooled to room temperature and analyzed using GC.

TABLE 18

Catalytic systems for the reaction between MAAH and PO in Table 17

| Nr. | Catalyst/co-catalyst | | |
|---|---|---|---|
| 1 | 0.0106 g Y(CF$_3$SO$_3$)$_3$ | 0.1 mol.-% | rel. to PO |
|   | 0.0911 g TEBAC | 2 mol.-% | rel. to PO |
|   | 0.0318 g Cr(III) solution | 0.75 wt % | rel. to entire batch |
| 2 | 0.0116 g La(CF$_3$SO$_3$)$_3$ | 0.1 mol.-% | rel. to PO |
|   | 0.0911 g TEBAC | 2 mol.-% | rel. to PO |
|   | 0.0318 g Cr(III) solution | 0.75 wt % | rel. to entire batch |
| 3 | 0.0123 g Yb(CF$_3$SO$_3$)$_3$ | 0.1 mol.-% | rel. to PO |
|   | 0.0456 g TEBAC | 2 mol.-% | rel. to PO |
|   | 0.0318 g Cr(III) solution | 0.75 wt % | rel. to entire batch |
| 4 | 0.0098 g Sc(SO$_3$CF$_3$)$_3$ | 0.1 mol.-% | rel. to PO |
|   | 0.0456 g TEBAC | 2 mol.-% | rel. to PO |
|   | 0.0318 g Cr(III) solution | 0.75 wt % | rel. to entire batch |
| 5 | 0.0121 g Dy(CF$_3$SO$_3$)$_3$ | 0.1 mol.-% | rel. to PO |
|   | 0.0456 g TEBAC | 2 mol.-% | rel. to PO |
|   | 0.0318 g Cr(III) solution | 0.75 wt % | rel. to entire batch |
| 6 | 0.0117 g Pr(CF$_3$SO$_3$)$_3$ | 0.1 mol.-% | rel. to PO |
|   | 0.0456 g TEBAC | 2 mol.-% | rel. to PO |
|   | 0.0318 g Cr(III) solution | 0.75 wt % | rel. to entire batch |

TABLE 19

Catalyst combinations tested for the reaction between MAAH and PO

| Ex. | Catalytic system from Table 4 | Color | Comment | MAAH GC area-% | PO GC area-% | Product GC area-% |
|---|---|---|---|---|---|---|
| 15 | 1 | green | solids precipitated | 0.0772 | 1.112 | 90.97 |
| 16 | 2 | green | solids precipitated | 0.0759 | 1.044 | 91.05 |
| 17 | 3 | green | solids precipitated | 0.1337 | 1.163 | 89.36 |
| 18 | 4 | green | solids precipitated | 0.0775 | 1.025 | 91.09 |
| 17 | 5 | green | solids precipitated | 0.1404 | 1.131 | 88.07 |
| 18 | 6 | green | solids precipitated | 0.1328 | 1.044 | 88.87 |

The results show that Magnesium bromide in the catalytic system can be replaced by rare earth triflates without noticeable change in observed product yields.

The invention claimed is:

1. A process for preparation of a diester of general Formula (I):

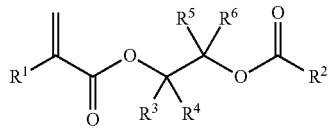

wherein:
R$^1$ is a hydrogen atom or a methyl group;
R$^2$ to R$^6$ are independently selected from hydrogen atoms or optionally substituted aliphatic or aromatic substituents having up to 17 carbon atoms;
wherein the process comprises at least process step (a):
(a) reacting a (meth)acrylic anhydride of general Formula (II):

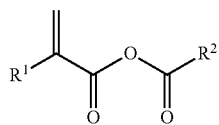

with an epoxide of general Formula (III):

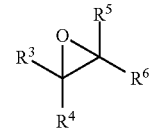

to deliver a product mixture comprising the diester of general Formula (I);
wherein the reaction is carried out in the presence of a catalyst in combination with a co-catalyst, wherein:
the catalyst comprises a first catalyst, a second catalyst or a combination of both, and:
the first catalyst is a halide of magnesium or a trifluoromethanesulfonate of a rare earth element; and
the second catalyst is a chromium (III) salt;
the co-catalyst is selected from the group consisting of: a tertiary amine; a quaternary ammonium salt; a tertiary phosphine; and a quaternary phosphonium salt.

2. The process of claim 1, wherein:
R$^1$ is a hydrogen atom, R$^2$ is a vinyl group, and the (meth)acrylic anhydride of formula (II) is acrylic acid anhydride; or alternatively:
R$^1$ is a methyl group, R$^2$ is a 1-methylvinyl group and the (meth)acrylic anhydride of formula (II) is methacrylic acid anhydride.

3. The process of claim 1, wherein the optionally substituted aliphatic or aromatic substituents having up to 17 carbon atoms are selected from the group consisting of:
optionally substituted alkyl, cycloalkyl, alkenyl, or alkadienyl substituents having up to 17 carbon atoms optionally substituted with one substituent R$^7$ selected from: a halogen atom, —CN, —SCN, —OCN, and —NCO.

4. The process of claim 1, wherein the epoxide of general Formula (III) is selected from the group consisting of: ethylene oxide; propylene oxide; 1-hexene oxide; cyclohexene oxide; cyclopentene oxide; 1-butene oxide; 2-butene oxide; isobutene oxide; styrene oxide; and glycidyl methacrylate.

5. The process of claim 1, wherein process step (a) is carried out in the presence of the first catalyst, the second catalyst and the co-catalyst.

6. The process of claim 1, wherein the co-catalyst is a quaternary ammonium salt.

7. The process of claim 1, wherein the co-catalyst is selected from the group consisting of: tetrabutylammonium chloride; tetrabutylammonium bromide; tetraethylammonium chloride; tetrabutylammonium acetate; tetramethylammonium chloride; tetrapentylammonium bromide; cetyl-trimethylammonium bromide; 1-butyl-3-methyl-imidazolyl chloride; cetylpyridinium chloride; and triethylbenzylammonium chloride.

8. The process of claim 1, wherein the second catalyst is a chromium (III) carboxylate.

9. The process of claim 8, wherein the chromium (III) carboxylate is selected from the group consisting of: chromium (III) 2-ethylhexanoate; chromium (III) heptanoate; chromium (III) acetate; and chromium (III) methacrylate.

10. The process of claim 1, wherein the total amount of the first catalyst in process step (a) is between 0.001 mol.-% and 10 mol.-%, based on the amount of the epoxide of general Formula (III).

11. The process of claim 1, wherein the total amount of the second catalyst in process step (a) is between 0.001 mol.-% and 10 mol.-%, based on the amount of the epoxide of general Formula (III).

12. The process of claim 1, wherein the total amount of the co-catalyst in process step (a) is between 0.001 mol.-% and 10 mol.-%, based on the amount of the epoxide of general Formula (III).

13. The process of claim 1, wherein the molar ratio anhydride of the general Formula (II): epoxide of the general Formula (III) in process step (a) is between 5:1 and 1:0.1.

14. The process of claim 1, wherein the temperature during process step (a) is in the range 20° C. to 140° C.

15. The process of claim 1, wherein the process is carried out in the presence of at least 10 mol % excess of the anhydride.

16. The process of claim 15, further comprising process steps (b) and (c) which are carried out after process step (a):
  (b) adding an auxiliary alcohol to the product mixture obtained in process step (a) to form a product mixture comprising the diester of the general Formula (I) and an ester of the auxiliary alcohol; and
  (c) removing of the ester of the auxiliary alcohol from the product mixture obtained in process step (b);
  wherein the auxiliary alcohol is a primary or secondary alcohol having a boiling point of not more than 150° C., measured at a pressure of $10^5$ Pa.

17. The process of claim 16, wherein, in process step (c), the ester of the auxiliary alcohol is removed from the product mixture by distillation.

18. The process of claim 17, wherein, in process step (a) the epoxide of general Formula (III) is selected from the group consisting of: ethylene oxide; propylene oxide; 1-hexene oxide; cyclohexene oxide; cyclopentene oxide; 1-butene oxide; 2-butene oxide; isobutene oxide; styrene oxide; and glycidyl methacrylate.

19. The process of claim 18, wherein process step (a) is carried out in the presence of the first catalyst, the second catalyst and the co-catalyst.

20. The process of claim 19, wherein the co-catalyst is selected from the group consisting of: tetrabutylammonium chloride; tetrabutylammonium bromide; tetraethylammonium chloride; tetrabutylammonium acetate; tetramethylammonium chloride; tetrapentylammonium bromide; cetyl-trimethylammonium bromide; 1-butyl-3-methyl-imidazolyl chloride; cetylpyridinium chloride; and triethylbenzylammonium chloride; and the second catalyst is a chromium (III) carboxylate.

* * * * *

UNITED STATES PATENT AND TRADEMARK OFFICE
CERTIFICATE OF CORRECTION

PATENT NO. : 11,319,276 B2
APPLICATION NO. : 17/268465
DATED : May 3, 2022
INVENTOR(S) : Treskow et al.

It is certified that error appears in the above-identified patent and that said Letters Patent is hereby corrected as shown below:

In the Specification

Column 10, Line 57, --THE-- is corrected to read --THF--,

Column 17, Line 21, --THE-- is corrected to read --THF--,

Column 17, Line 40, --THE-- is corrected to read --THF--.

Signed and Sealed this
Thirteenth Day of June, 2023

Katherine Kelly Vidal
*Director of the United States Patent and Trademark Office*